United States Patent
Dellinger et al.

(10) Patent No.: US 7,385,050 B2
(45) Date of Patent: Jun. 10, 2008

(54) CLEAVABLE LINKER FOR POLYNUCLEOTIDE SYNTHESIS

(75) Inventors: Douglas J Dellinger, Boulder, CO (US); Geraldine F Dellinger, Boulder, CO (US); Marvin H Caruthers, Loveland, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 436 days.

(21) Appl. No.: 10/652,063

(22) Filed: Aug. 30, 2003

(65) Prior Publication Data
US 2005/0048497 A1 Mar. 3, 2005

(51) Int. Cl.
C07H 21/00 (2006.01)
C07H 19/10 (2006.01)
C07H 19/20 (2006.01)

(52) U.S. Cl. .............. 536/25.3; 536/25.31; 536/25.33; 536/25.34; 536/26.6; 536/26.7; 536/27.6; 536/27.81; 536/28.5; 536/28.53

(58) Field of Classification Search .............. 536/25.3, 536/25.31, 25.33, 26.7, 26.8, 27.6, 27.81, 536/28.5, 25.34, 28.53
See application file for complete search history.

(56) References Cited

U.S. PATENT DOCUMENTS

| | | | |
|---|---|---|---|
| 4,500,707 A * | 2/1985 | Caruthers et al. | 536/25.34 |
| 4,668,777 A * | 5/1987 | Caruthers et al. | 536/25.5 |
| 6,222,030 B1 * | 4/2001 | Dellinger et al. | 536/25.3 |
| 6,258,454 B1 * | 7/2001 | Lefkowitz et al. | 428/333 |
| 6,630,581 B2 * | 10/2003 | Dellinger et al. | 536/22.1 |
| 2002/0045221 A1 | 4/2002 | Dellinger et al. | |
| 2002/0058802 A1 * | 5/2002 | Dellinger et al. | 536/25.31 |
| 2003/0129589 A1 | 7/2003 | Koster et al. | |

FOREIGN PATENT DOCUMENTS

| | | |
|---|---|---|
| EP | 0241363 | 10/1987 |
| EP | 1428810 A2 | 6/2004 |
| WO | WO92/10092 | 6/1992 |

OTHER PUBLICATIONS

Mishra, Rakesh K. et al., "Protecting groups as purification tool in large-scale synthesis of small oligodeoxyribonucleotides", Indian Journal of Chemistry, 1988, 27B(9), 817-820.
Sekine et al., "Synthesis of Oligodeoxyribonucleotides Involving a Rapid Procedure for Removal of Base-Protecting Groups by Use of the 4,4', 4"—Tris(benzoyloxy) trityl (TBTr) Group", Bull. Chem. Soc. Japan, vol. 59, pp. 1781-1789, (1986).
Kamimura et al., "Synthesis of Dodecaribonuecleotide, GUAUCAAUAAUG, by Use of "Fully" Protected ribonucleotide Building Blocks", J. Am. Chem. Soc. 1984, vol. 106, 4552-4557.
Nyilas A., et al., "Synthesis of [3'(O)-5'(C)]Oxyacetamido Linked Nucleotides", Tetrahedron, vol. 46, No. 6, 1990, pp. 2149-2164.
Sekine, et al., "Introduction of the 4, 4', 4"-Tris (Benzoyloxy)trityl group into the Exo Amino groups of deoxyribonucleotides and its properties" Tetrahedron, vol. 41, No. 23, 1985, pp. 5445-5453.
Sekine, et al., "Synthesis of Short Oligoribonucleotides bearing a 3'—or 5'—terminal phosphate by use of 4, 4", 4"-tris (4, 5-dichlorophtalimido)trityl) as a new 5' -hydroxyl protecting group" J. Amer. Chem. Society, vol. 108, 1986, pp. 4581-4586.
Will et al., "The Synthesis of Polamide Nucleic Acids using a Novel Monomethoxytrityl Protecting-Group Strategy", Tetrahedron, vol. 51, No. 44, pp. 12069-12082, 1985.
Katzhendler et al., "The Effect of Spacer, Linkage and Solid Support on the Synthesis of Oligonucleotides", Tetrahedron, vol. 45, No. 9, pp. 2777-2792, 1989.
Iwase et al, "A New Method for the Synthesis of Capped Oligoribonucleotides by Use of an Appropriately Protected 7-Methylguanosine Diphosphate Derivative as a Donor for the Triphosphate Derivative as a Donor for the Triphosphate Bond Formation", Tetrahedron Letters, vol. 29, No. 24, pp. 2969-2972, 1988.

* cited by examiner

*Primary Examiner*—L. E. Crane

(57) ABSTRACT

Functionalized supports for polynucleotide synthesis are disclosed. The supports have linker moieties that are stable to conditions used in polynucleotide synthesis, but may be cleaved to release synthesized polynucleotides from the support. Methods of making the functionalized supports and methods of using are also disclosed. In particular embodiments of methods of making the functionalized supports, a solid support, on which an available reactive group is bound, is contacted with a reagent having the structure (I)

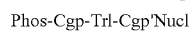

Phos-Cgp-Trl-Cgp'Nucl          (I)

wherein the groups are defined as follows:
Phos is a reactive phosphorus group capable of specifically reacting with an available reactive group on the support,
Trl is a triaryl methyl linker group having three aryl groups, each bound to a central methyl carbon, at least one of said three aryl groups having one or more substituents,
Cgp is a linking group linking the reactive phosphorus group and the triaryl methyl linker group, or is a bond linking the reactive phosphorus group and the triaryl methyl linker group,
Nucl is a nucleoside moiety, wherein the nucleoside moiety is optionally part of a polynucleotide moiety, and
Cgp' is a linking group linking the nucleoside moiety and the triaryl methyl linker group, or is a bond linking the nucleoside moiety and the triaryl methyl linker group.
In typical embodiments, the solid support is contacted with the reagent having the structure (I) under conditions and for a time sufficient to result in a functionalized support having a nucleoside moiety bound to the solid support via a triaryl methyl linker group.

21 Claims, 2 Drawing Sheets

CLEAVABLE LINKER FOR POLYNUCLEOTIDE SYNTHESIS

STATEMENT REGARDING FEDERALLY SPONSORED RESEARCH OR DEVELOPMENT

This invention was made with Government support under Agreement No. N39998-01-9-7068. The Government has certain rights in the invention.

RELATED APPLICATIONS

Related subject matter is disclosed in U.S. patent applications entitled "Method for Polynucleotide Synthesis", (Ser. No. 10/652054; "Method of Polynucleotide Synthesis Using Modified Support", (Ser. No. 10/652049); "Exocyclic Amine Triaryl Methyl Protecting Groups in Two-Step Polynucleotide Synthesis" (Ser. No. 10/652064, now U.S. Pat. No. 7,193,077); "Precursors For Two-Step Polynucleotide Synthesis" (Ser. No. 10/652048); all applications filed in the names of Dellinger et al. on Aug. 30, 2003, the same day as the instant application, all of which are incorporated herein by reference in their entireties, provided that, if a conflict in definition of terms arises, the definitions provided in the present application shall be controlling.

DESCRIPTION

1. Field of the Invention

The invention relates generally to nucleic acid chemistry and to the chemical synthesis of polynucleotides. More particularly, the invention relates to modifying a support for use in polynucleotide synthesis to provide for release of the synthesized polynucleotides from the support. The invention is useful in the manufacture of reagents and devices used in the fields of biochemistry, molecular biology and pharmacology, and in medical diagnostic and screening technologies.

2. Background of the Invention

Solid phase chemical synthesis of DNA fragments is routinely performed using protected nucleoside phosphoramidites. Beaucage et al. (1981) Tetrahedron Lett. 22:1859. In this approach, the 3'-hydroxyl group of an initial 5'-protected nucleoside is first covalently attached to the polymer support. Pless et al. (1975) Nucleic Acids Res. 2:773. Synthesis of the oligonucleotide then proceeds by deprotection of the 5'-hydroxyl group of the attached nucleoside, followed by coupling of an incoming nucleoside-3'-phosphoramidite to the deprotected hydroxyl group. Matteucci et al. (1981) J. Am. Chem. Soc. 103:3185. The resulting phosphite triester is finally oxidized to a phosphotriester to complete one round of the synthesis cycle. Letsinger et al. (1976) J. Am. Chem. Soc. 98:3655. The steps of deprotection, coupling and oxidation are repeated until an oligonucleotide of the desired length and sequence is obtained. This process is illustrated schematically in FIG. 1 (wherein "B" represents a purine or pyrimidine base, "DMT" represents dimethoxytrityl and "iPR" represents isopropyl). Optionally, after the coupling step, the product may be treated with a capping agent designed to esterify failure sequences and cleave phosphite reaction products on the heterocyclic bases.

The chemical group conventionally used for the protection of nucleoside 5'-hydroxyls is dimethoxytrityl, which is removable with acid. Khorana (1968) Pure Appl. Chem. 17:349; Smith et al. (1962) J. Am. Chem. Soc. 84:430. This acid-labile protecting group provides a number of advantages for working with both nucleosides and oligonucleotides. For example, the DMT group can be introduced onto a nucleoside regioselectively and in high yield. Brown et al. (1979) Methods in Enzymol. 68:109. Also, the lipophilicity of the DMT group greatly increases the solubility of nucleosides in organic solvents, and the carbocation resulting from acidic deprotection gives a strong chromophore, which can be used to indirectly monitor coupling efficiency. Matteucci et al. (1980) Tetrahedron Lett. 21:719. In addition, the hydrophobicity of the group can be used to aid separation on reverse-phase HPLC. Becker et al. (1985) J. Chromatogr. 326:219.

However, the use of DMT as a hydroxyl-protecting group for conventional oligonucleotide synthesis has a number of perceived drawbacks. The N-glycosidic linkages of oligodeoxyribonucleotides are susceptible to acid catalyzed cleavage (Kochetkov et al., Organic Chemistry of Nucleic Acids (New York: Plenum Press, 1972)), and even when the protocol is optimized, recurrent removal of the DMT group with acid during oligonucleotide synthesis results in depurination. Shaller et al. (1963) J. Am. Chem. Soc. 85:3821. The N-6-benzoyl-protected deoxyadenosine nucleotide is especially susceptible to glycosidic cleavage, resulting in a substantially reduced yield of the final oligonucleotide. Efcavitch et al. (1985) Nucleosides & Nucleotides 4:267. Attempts have been made to address the problem of acid-catalyzed depurination utilizing alternative mixtures of acids and various solvents; see, for example, Sonveaux (1986) Bioorganic Chem. 14:274. However, this approach has met with limited success. McBride et al. (1986) J. Am. Chem. Soc. 108:2040. Also, using the conventional synthesis scheme set forth in FIG. 1 requires additional steps per cycle of addition of a nucleotide to the growing polynucleotide chain, including the post-coupling deprotection step in which the DMT group is removed following oxidation of the internucleotide phosphite triester linkage to a phosphotriester.

The problems associated with the use of DMT are exacerbated in solid phase oligonucleotide synthesis where "microscale" parallel reactions are taking place on a very dense, packed surface. Applications in the field of genomics and high throughput screening have fueled the demand for precise chemistry in such a context. Side-reactions, which are known to occur at detectable but acceptable levels during routine synthesis, can rise to unacceptable levels under the conditions required for these expanded applications. Thus, increasingly stringent demands are placed on the chemical synthesis cycle as it was originally conceived, and the problems associated with conventional methods for synthesizing oligonucleotides are rising to unacceptable levels in these expanded applications.

Recently, alternate schemes for synthesis of polynucleotides have been described. See, e.g. U.S. Pat. No. 6,222,030 to Dellinger et al., U.S. Pat. Appl'n Publ'n No. US2002/0058802 A1 to Dellinger et al., Seio et al. (2001) Tetrahedron Lett. 42 (49):8657-8660. These schemes involve protecting groups other than DMT at the 3' or 5' positions and correspondingly different conditions for performing reactions such as deprotection at the 3' or 5' positions. These schemes have the additional advantage of reducing the number of steps required per cycle of addition of a nucleotide to the growing polynucleotide chain. FIG. 2 illustrates such a process having a two-step synthesis cycle, represented in FIG. 2 as a coupling step and a simultaneous deprotection and oxidation step.

In previously reported methods such as that shown in FIG. 1, the newly synthesized oligonucleotides containing N-protected nucleobases are typically deprotected using displacement by nucleophiles such as ammonia or methylamine. These reagents can have similar properties to (and thus may not be compatible with) the reagents used for the alternative removal of 3' or 5' protecting groups in simplified 2-step DNA synthesis.

Solid phase polynucleotide synthesis results in a polynucleotide bound upon a solid support. Typically, an additional step releases the polynucleotide from the solid support after the polynucleotide strand has been synthesized. This release step yields the polynucleotide in solution, which may then be separated from the solid support, e.g. by filtration or other suitable methods. The release step is dependent upon having a support that is functionalized with a releasable moiety that, while inert under the conditions used in the synthesis cycle, provides for the release of the synthesized polynucleotide under conditions conducive for doing so.

What is needed is an improved method for the synthesis of polynucleotides providing for the release of the synthesized polynucleotide from the support.

SUMMARY OF THE INVENTION

The invention addresses the aforementioned deficiencies in the art, and provides novel cleavable linkers for use in the synthesis of polynucleotides. In a method in accordance with the invention, a functionalized support having a cleavable linker group is prepared. In the method, a solid support, on which an available reactive group is bound, is contacted with a reagent having the structure (I)

under conditions and for a time sufficient to result in a functionalized support having a nucleoside moiety bound to the solid support via a triaryl methyl linker group.

In some embodiments, the method further comprises contacting the functionalized support with a combined oxidation/deprotection agent.

The reagent employed in the current invention typically has the structure (I)

wherein the groups are defined as follows:

Phos is a reactive phosphorus group capable of specifically reacting with an available reactive group on the support, Trl is a triaryl methyl linker group having three aryl groups, each bound to a central methyl carbon, at least one of said three aryl groups having one or more substituents, Cgp is a linking group linking the reactive phosphorus group and the triaryl methyl linker group, or is a bond linking the reactive phosphorus group and the triaryl methyl linker group, Nucl is a nucleoside moiety, wherein the nucleoside moiety is optionally part of a polynucleotide moiety, and Cgp' is a linking group linking the nucleoside moiety and the triaryl methyl linker group, or is a bond linking the nucleoside moiety and the triaryl methyl linker group.

The present invention provides reagents having the structure (I). The present invention further provides methods of making functionalized supports for polynucleotide synthesis using reagents having the structure (I) as described herein. A functionalized support in accordance with the invention comprises a nucleoside moiety attached to a solid support via a triaryl methyl linker group, wherein the triaryl methyl linker group is attached to the solid support via a phosphorus-containing linkage group, e.g. a phosphite group or a phosphate group.

A functionalized support having a cleavable linker group formed in accordance with the present invention typically has the structure (II)

Wherein the groups are defined as follows:

◯- is a solid support,

Trl, Cgp', and Nucl are as defined above,

Plg is a phosphorus-containing linkage group, e.g. a phosphite group or a phosphate group, and Cgp" is a linking group linking the phosphorus-containing linkage group and the triaryl methyl linker group, or is a bond linking the phosphorus-containing linkage group and the triaryl methyl linker group.

Further information about the groups described above, reagents having the structure (I), functionalized supports having the structure (II), and use of such reagents in making functionalized supports is described herein. The use of a triaryl methyl linker group allows polynucleotides synthesized upon the functionalized support to be released from the solid support under acidic conditions.

Additional objects, advantages, and novel features of this invention shall be set forth in part in the descriptions and examples that follow and in part will become apparent to those skilled in the art upon examination of the following specifications or may be learned by the practice of the invention. The objects and advantages of the invention may be realized and attained by means of the materials and methods particularly pointed out in the appended claims.

BRIEF DESCRIPTION OF THE DRAWINGS

These and other features of the invention will be understood from the description of representative embodiments of the method herein and the disclosure of illustrative materials for carrying out the method, taken together with the Figures, wherein FIG. 1 schematically illustrates prior art synthesis of polynucleotides.

To facilitate understanding, identical reference numerals/designations have been used, where practical, to designate corresponding elements that are common to the Figures. Figure components are not drawn to scale.

DETAILED DESCRIPTION

Figure 1:
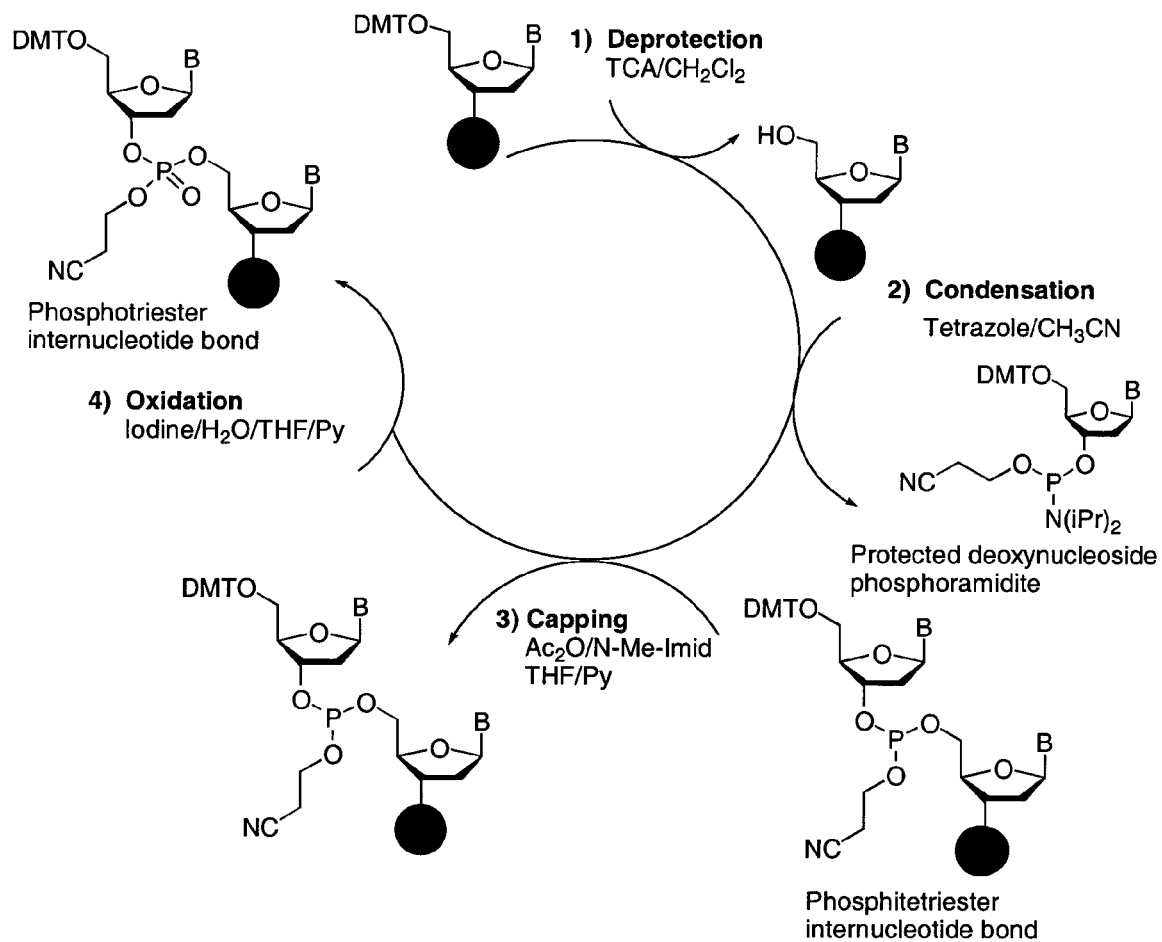

Before the invention is described in detail, it is to be understood that unless otherwise indicated this invention is not limited to particular materials, reagents, reaction materials, manufacturing processes, or the like, as such may vary. It is also to be understood that the terminology used herein is for purposes of describing particular embodiments only, and is not intended to be limiting. It is also possible in the present invention that steps may be executed in different sequence where this is logically possible. However, the sequence described below is preferred.

It must be noted that, as used in the specification and the appended claims, the singular forms "a," "an" and "the" include plural referents unless the context clearly dictates otherwise. Thus, for example, reference to "an insoluble support" includes a plurality of insoluble supports. Similarly, reference to "a substituent", as in a compound substituted with "a substituent", includes the possibility of substitution with more than one substituent, wherein the substituents may be the same or different. In this specification and in the claims that follow, reference will be made to a number of terms that shall be defined to have the following meanings unless a contrary intention is apparent:

A "nucleotide" refers to a sub-unit of a nucleic acid (whether DNA or RNA or analogue thereof) which includes a phosphate group, a sugar group and a heterocyclic base, as well as analogs of such sub-units. A "nucleoside" references a nucleic acid subunit including a sugar group and a heterocyclic base. A "nucleoside moiety" refers to a portion of a molecule having a sugar group and a heterocyclic base (as in a nucleoside); the molecule of which the nucleoside moiety is a portion may be, e.g. a polynucleotide, oligonucleotide, or nucleoside phosphoramidite. A "nucleotide monomer" refers to a molecule which is not incorporated in a larger oligo- or poly-nucleotide chain and which corresponds to a single nucleotide sub-unit; nucleotide monomers may also have activating or protecting groups, if such groups are necessary for the intended use of the nucleotide monomer. A "polynucleotide intermediate" references a molecule occurring between steps in chemical synthesis of a polynucleotide, where the polynucleotide intermediate is subjected to further reactions to get the intended final product, e.g. a phosphite intermediate which is oxidized to a phosphate in a later step in the synthesis, or a protected polynucleotide which is then deprotected. An "oligonucleotide" generally refers to a nucleotide multimer of about 2 to 200 nucleotides in length, while a "polynucleotide" includes a nucleotide multimer having at least two nucleotides and up to several thousand (e.g. 5000, or 10,000) nucleotides in length. It will be appreciated that, as used herein, the terms "nucleoside", "nucleoside moiety" and "nucleotide" will include those moieties which contain not only the naturally occurring purine and pyrimidine bases, e.g., adenine (A), thymine (T), cytosine (C), guanine (G), or uracil (U), but also modified purine and pyrimidine bases and other heterocyclic bases which have been modified (these moieties are sometimes referred to herein, collectively, as "purine and pyrimidine bases and analogs thereof"). Such modifications include, e.g., methylated purines or pyrimidines, acylated purines or pyrimidines, and the like, or the addition of a protecting group such as acetyl, difluoroacetyl, trifluoroacetyl, isobutyryl, benzoyl, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl) uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "modified alkyl" refers to an alkyl group having from one to twenty-four carbon atoms, and further having additional groups, such as one or more linkages selected from ether-, thio-, amino-, phospho-, oxo-, ester-, and amido-, and/or being substituted with one or more additional groups including lower alkyl, aryl, alkoxy, thioalkyl, hydroxyl, amino, sulfonyl, thio, mercapto, imino, halo, cyano, nitro, nitroso, azido, carboxy, sulfide, sulfone, sulfoxy, phosphoryl, silyl, silyloxy, and boronyl. The term "modified lower alkyl" refers to a group having from one to six carbon atoms and further having additional groups, such as one or more linkages selected from ether-, thio-, amino-, phospho-, keto-, ester- and amido-, and/or being substituted with one or more groups including lower alkyl; aryl, alkoxy, thioalkyl, hydroxyl, amino, sulfonyl, thio, mercapto, imino, halo, cyano, nitro, nitroso, azido, carboxy, sulfide, sulfone, sulfoxy, phosphoryl, silyl, silyloxy, and boronyl. The term "alkoxy" as used herein refers to a substituent —O—R wherein R is alkyl as defined above. The term "lower alkoxy" refers to such a group wherein R is lower alkyl. The term "thioalkyl" as used herein refers to a substituent —S—R wherein R is alkyl as defined above.

The term "alkenyl" as used herein, unless otherwise specified, refers to a branched, unbranched or cyclic (e.g. in the case of $C_5$ and $C_6$) hydrocarbon group of 2 to 24, typically 2 to 12, carbon atoms containing at least one double bond, such as ethenyl, vinyl, allyl, octenyl, decenyl, and the like. The term "lower alkenyl" intends an alkenyl group of two to six carbon atoms, and specifically includes vinyl and allyl. The term "cycloalkenyl" refers to cyclic alkenyl groups.

The term "alkynyl" as used herein, unless otherwise specified, refers to a branched or unbranched hydrocarbon group of 2 to 24, typically 2 to 12, carbon atoms containing at least one triple bond, such as acetylenyl, ethynyl, n-propynyl, isopropynyl, n-butynyl, isobutynyl, t-butynyl, octynyl, decynyl and the like. The term "lower alkynyl" intends an alkynyl group of two to six carbon atoms, and includes, for example, acetylenyl and propynyl, and the term "cycloalkynyl" refers to cyclic alkynyl groups.

The term "aryl" as used herein refers to an aromatic species containing 1 to 5 aromatic rings, either fused or linked, and either unsubstituted or substituted with 1 or more substituents typically selected from the group consisting of lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxylthio, mercapto, amino, imino, halo, cyano, nitro, nitroso, azido, carboxy, sulfide, sulfone, sulfoxy, phosphoryl, silyl, silyloxy, and boronyl. Typical aryl groups contain 1 to 3 fused aromatic rings, and more typical aryl groups contain 1 aromatic ring or 2 fused aromatic rings. Aromatic groups herein may or may not be heterocyclic. The term "aralkyl" intends a moiety containing both alkyl and aryl species, typically containing less than about 24 carbon atoms, and more typically less than about 12 carbon atoms in the alkyl segment of the moiety, and typically containing 1 to 5 aromatic rings. The term "aralkyl" will usually be used to refer to aryl-substituted alkyl groups. The term "aralkylene" will be used in a similar manner to refer to moieties containing both alkylene and aryl species, typically containing less than about 24 carbon atoms in the alkylene portion and 1 to 5 aromatic rings in the aryl portion, and typically aryl-substituted alkylene. Exemplary aralkyl groups have the structure —$(CH_2)_j$—Ar wherein j is an integer in the range of 1 to 24, more typically 1 to 6, and Ar is a monocyclic aryl moiety.

The term "electron withdrawing" denotes the tendency of a substituent to attract valence electrons of the molecule of which it is a part, i.e., an electron-withdrawing substituent is electronegative.

The term "alpha effect," as in an "alpha effect nucleophile" in a deprotection/oxidation agent, is used to refer to an enhancement of nucleophilicity that is found when the atom adjacent a nucleophilic site bears a lone pair of electrons. As the term is used herein, a nucleophile is said to exhibit an "alpha effect" if it displays a positive deviation from a Bronsted-type nucleophilicity plot. Hoz et al. (1985) Israel J. Chem. 26:313. See also, Aubort et al. (1970) Chem. Comm. 1378; Brown et al. (1979) J. Chem. Soc. Chem. Comm.171; Buncel et al. (1982) J. Am. Chem. Soc. 104: 4896; Edwards et al. (1962) J. Am. Chem. Soc. 84:16; Evanseck et al. (1987) J. Am. Chem Soc. 109:2349. The magnitude of the alpha effect is dependent upon the electrophile which is paired with the specific nucleophile. McIsaac, Jr. et al. (1972), J. Org. Chem. 37:1037. Peroxy anions are example of nucleophiles which exhibit strong alpha effects.

The term "heterocyclic" refers to a five- or six-membered monocyclic structure or to an eight- to eleven-membered bicyclic structure which is either saturated or unsaturated. The heterocyclic groups herein may be aliphatic or aromatic. Each heterocyclic group consists of carbon atoms and from one to four heteroatoms selected from the group consisting of nitrogen, oxygen and sulfur. As used herein, the term "nitrogen heteroatoms" includes any oxidized form of nitrogen and the quaternized form of nitrogen. The term "sulfur heteroatoms" includes any oxidized form of sulfur. Examples of heterocyclic groups include purine, pyrimidine, piperidinyl, morpholinyl and pyrrolidinyl. "Heterocyclic base" refers to any natural or non-natural heterocyclic moiety that can participate in base pairing or base stacking interaction on an oligonucleotide strand.

"Exocyclic" refers to a group situated outside of the ring of a cyclic chemical structure, e.g. a portion of a substituent of the ring is exocyclic to the ring. As used herein, exocyclic amine refers to an amine group that is a substituent of a ring of a heterocyclic base and includes embodiments in which the nitrogen of the amine group is attached directly to a member of the ring structure and also includes embodiments in which the nitrogen of the amine group may be linked to the ring structure of the heterocyclic base via an intervening group.

An "internucleotide bond" refers to a chemical linkage between two nucleoside moieties, such as a phosphodiester linkage in nucleic acids found in nature, or such as linkages well known from the art of synthesis of nucleic acids and nucleic acid analogues. An internucleotide bond may comprise a phospho or phosphite group, and may include linkages where one or more oxygen atoms of the phospho or phosphite group are either modified with a substituent or replaced with another atom, e.g. a sulfur atom or the nitrogen atom of a mono- or di-alkyl amino group.

"Moiety" and "group" are used interchangeably herein to refer to a portion of a molecule, typically having a particular functional or structural feature, e.g. a linking group (a portion of a molecule connecting two other portions of the molecule), or an ethyl moiety (a portion of a molecule with a structure closely related to ethane). A "triaryl methyl linker group" as used herein references a triaryl methyl group having one or more substituents on the aromatic rings of the triaryl methyl group, wherein the triaryl methyl group is bonded to two other moieties such that the two other moieties are linked via the triaryl methyl group.

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—). "Phosphorus-containing linkage group" references a moiety having a phospho linkage, wherein the moiety is bonded to two other moieties, wherein the two other moieties are linked via the moiety having the phospho linkage. Typical phosphorus-containing linkage groups include phosphite groups (including phosphite esters), and phosphate groups (including phosphate esters), as well as other moieties having a phospho linkage.

"Bound" may be used herein to indicate direct or indirect attachment. In the context of chemical structures, "bound" (or "bonded") may refer to the existence of a chemical bond directly joining two moieties or indirectly joining two moieties (e.g. via a linking group). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect.

"Functionalized" references a process whereby a material is modified to have a specific moiety bound to the material, e.g. a molecule or substrate is modified to have the specific moiety; the material (e.g. molecule or support) that has been so modified is referred to as a functionalized material (e.g. functionalized molecule or functionalized support).

The term "halo" or "halogen" is used in its conventional sense to refer to a chloro, bromo, fluoro or iodo substituent.

By "protecting group" as used herein is meant a species which prevents a portion of a molecule from undergoing a specific chemical reaction, but which is removable from the molecule following completion of that reaction. This is in contrast to a "capping group," which permanently binds to a segment of a molecule to prevent any further chemical transformation of that segment. A "hydroxyl protecting group" refers to a protecting group where the protected group is a hydroxyl. "Reactive site hydroxyl" references a hydroxyl group capable of reacting with an activated nucleotide monomer to result in an internucleotide bond being formed. In typical embodiments, the reactive site hydroxyl is the terminal 5'-hydroxyl during 3'-5' polynucleotide synthesis and is the 3'-hydroxyl during 5'-3' polynucleotide synthesis. An "acid labile protected hydroxyl" is a hydroxyl group protected by a protecting group that can be removed by acidic conditions. Similarly, an "acid stabile protected hydroxyl" is a hydroxyl group protected by a protecting group that is not removed (is stabile) under acidic conditions. An "acid labile linking group" is a linking group that releases a linked group under acidic conditions. A trityl group is a triphenyl methyl group, in which one or more of the phenyl groups of the triphenyl methyl group is optionally substituted. A "substituted trityl group" or a "substituted triphenyl methyl group" is a triphenyl methyl group on which one of the hydrogens of the phenyl groups of the triphenyl methyl group is replaced by a substituent.

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (typically a hydrogen) is replaced by the second group.

"Substituent" references a group that replaces another group in a chemical structure. Typical substituents include nonhydrogen atoms (e.g. halogens), functional groups (such as, but not limited to amino, sulfhydryl, carbonyl, hydroxyl, alkoxy, carboxyl, silyl, silyloxy, phosphate and the like), hydrocarbyl groups, and hydrocarbyl groups substituted with one or more heteroatoms. Exemplary substituents include alkyl, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, boronyl, and modified lower alkyl.

A "group" includes both substituted and unsubstituted forms. Typical substituents include one or more lower alkyl, modified alkyl, any halogen, hydroxy, or aryl. Any substituents are typically chosen so as not to substantially adversely affect reaction yield (for example, not lower it by more than 20% (or 10%, or 5% or 1%) of the yield otherwise obtained without a particular substituent or substituent combination). Hyphens, or dashes, are used at various points throughout this specification to indicate attachment, e.g. where two named groups are immediately adjacent a dash in the text, this indicates the two named groups are attached to each other. Similarly, a series of named groups with dashes between each of the named groups in the text indicates the named groups are attached to each other in the order shown. Also, a single named group adjacent a dash in the text indicates the named group is typically attached to some other, unnamed group. In some embodiments, the attachment indicated by a dash may be, e.g. a covalent bond between the adjacent named groups. In some other embodiments, the dash may indicate indirect attachment, i.e. with intervening groups between the named groups. At various points throughout the specification a group may be set forth in the text with or without an adjacent dash, (e.g. amido or amido-, further e.g. Trl or Trl-, yet further e.g. Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g. the Sugar group, herein; further e.g. where a linkage is intended, such as linking groups).

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present, and, thus, the description includes structures wherein a non-hydrogen substituent is present and structures wherein a non-hydrogen substituent is not present. At various points herein, a moiety may be described as being present zero or more times: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly. Similarly, a moiety may be described as being either (1) a group linking two adjacent groups, or (2) a bond linking the two adjacent groups: this is equivalent to the moiety being optional and includes embodiments in which the moiety is present and embodiments in which the moiety is not present. If the optional moiety is not present (is present in the structure zero times), adjacent groups described as linked by the optional moiety are linked to each other directly.

Accordingly, an embodiment in accordance with the invention is directed to a method for preparing functionalized supports such as may find use in polynucleotide synthesis. The embodiment comprises contacting a solid support, on which an available reactive group is bound, with a reagent having a reactive phosphorus group attached to a nucleoside moiety via a triaryl methyl linker group, the contacting being performed under conditions and for a time sufficient to result in the nucleoside moiety bound to the support via the triaryl methyl linker group, wherein the triaryl methyl linker group is bound to the support via a phosphorus-containing linkage group. The phosphorus-containing linkage group results from the reaction of the reactive phosphorus group with the available reactive group bound on the solid support. In the method, the functionalized support comprises a nucleoside moiety, a triaryl methyl linker group, and a solid support, the nucleoside moiety attached to the solid support via the triaryl methyl linker group.

In particular embodiments, the product of the above-described contacting step is then contacted with an oxidizing agent and/or a deprotecting agent. In certain embodiments, the product is contacted with a combined deprotection/oxidation agent, i.e. the deprotection and oxidation are performed concurrently. The deprotection agent serves to remove a hydroxylprotecting group from the product, thereby providing an available hydroxyl for polynucleotide synthesis. The oxidation agent serves to oxidize the phosphorus-containing linkage group, for example from phosphite to phosphate or from phosphite ester to phosphate ester.

The reagent provided in accordance with the current invention typically has the structure (I)

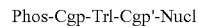

Phos-Cgp-Trl-Cgp'-Nucl    (I)

wherein the groups are defined as follows:

Phos is a reactive phosphorus group (e.g. a phosphoramidite group) capable of specifically reacting with an available reactive group on the support, Trl is a triaryl methyl linker group having three aryl groups, each bound to a central methyl carbon, at least one of said three aryl groups having one or more substituents, Cgp is a linking group linking the reactive phosphorus group and the triaryl methyl linker group, or is a bond linking the reactive phosphorus group and the triaryl methyl linker group, Nucl is a nucleoside moiety, wherein the nucleoside moiety is optionally part of a polynucleotide moiety, and Cgp' is a linking group linking the nucleoside moiety and the triaryl methyl linker group, or is a bond linking the nucleoside moiety and the triaryl methyl linker group.

Referring now to structure (I), the Phos group is a reactive phosphorus group capable of coupling to an available reactive group (e.g. a hydroxyl, a thio, or an amino group) bound to a solid support. A reactive phosphorus group in accordance with the present invention typically has the structure (VI)

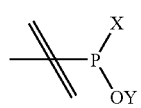

Wherein the groups are defined as follows:

The broken line indicates the bond via which the reactive phosphorus group is bound to the triarylmethyl linker group, typically via a linking group (Cgp) that is a substituent on one of the aryl rings of the triarylmethyl linker group.

X may be a halogen (particularly Cl or Br) or a secondary amino group, NQ1Q2. In certain embodiments the reactive phosphorus groups are phosphoramidites, where X is NQ1Q2, and in which Q1 and Q2 may be the same or different and are typically selected from the group consisting of alkyl, aryl, aralkyl, cycloalkyl, alkenyl, cycloalkenyl, alkynyl, cycloalkynyl, optionally containing one or more nonhydrocarbyl linkages such as ether linkages, thio linkages, oxo linkages, amine, azole, and imine linkages, and optionally substituted on one or more available carbon atoms with a nonhydrocarbyl substituent such as cyano, nitro, halo, or the like. Typically, Q1 and Q2 represent lower alkyl, more preferably sterically hindered lower alkyls such as isopropyl, t-butyl, isobutyl, sec-butyl, neopentyl, tert-pentyl, isopentyl, sec-pentyl, and the like. More typically, Q1 and Q2 both represent isopropyl. Alternatively, Q1 and Q2 may be linked to form a mono- or polyheterocyclic ring having a total of from 1 to 3, usually 1 to 2 heteroatoms and from 1 to 3 rings. In such a case, Q1 and Q2 together with the nitrogen atom to which they are attached represent, for example, pyrrolidone, morpholino or piperidino. Usually, Q1 and Q2 have a total of from 2 to 12 carbon atoms. Examples of specific —NQ1Q2 moieties thus include, but are not limited to, dimethylamine, diethylamine, diisopropylamine, dibutylamine, methylpropylamine, methylhexylamine, methylcyclopropylamine, ethylcyclohexylamine, methylbenzylamine, methylcyclohexylmethylamine, butylcyclohexylamine, morpholine, thiomorpholine, pyrrolidine, piperidine, 2,6-dimethylpiperidine, piperazine, and the like.

Y is typically hydrido or hydrocarbyl (including substituted hydrocarbyl), typically alkyl, alkenyl, aryl, aralkyl, or cycloalkyl. More typically, Y represents: lower alkyl; benzyl; substituted benzyl; electron-withdrawing β-substituted aliphatic, particularly electron-withdrawing β-substituted ethyl such as β-trihalomethyl ethyl, β-cyanoethyl, β-sulfoethyl, β-nitro-substituted ethyl, and the like; electron-withdrawing substituted phenyl, particularly halo-, sulfo-, cyano- or nitro-substituted phenyl; or electron-withdrawing substituted phenylethyl. Still more typically, Y represents methyl, β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, β-thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsilyl) ethyl, 2-methylthioethyl, 2-(diphenylphosphino)-ethyl, 1-methyl-1-phenylethyl, 3-buten-1-yl, 4-(trimethylsilyl)-2-buten-1-yl, cinnamyl, α-methylcinnamyl, and 8-quinolyl.

Under appropriate conditions as described herein, the reactive phosphorus group specifically reacts with an available reactive group bound to the solid support such that the desired product of the reaction is achieved in acceptable yield. In this regard, "specifically reacts" means that an acceptable amount of reactive phosphorus group reacts as described herein with the available reactive group bound to the solid support to result in the nucleoside moiety bound to the solid support (via the triaryl methyl linker moiety) in acceptable yield. In various embodiments, the acceptable yield is at least about 5%, at least about 10%, at least about 20%, at least about 30%, at least about 50%, or even more, where the percent indicated is the proportion of nucleoside moiety incorporated (in moles) over the theoretical amount of nucleoside moiety (in moles) that would be incorporated if the reaction was 100% completed, expressed as a percent. In particular embodiments, the reactive phosphorus group Phos may comprise a leaving group which is replaced by a portion of the solid support (e.g. a portion of a modification layer or functional group of the solid support) as a result of the reaction.

Referring to structure (I), the Trl-group is a substituted triaryl methyl linker group and has the structure (IV),

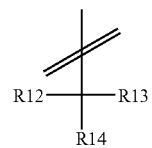

wherein the broken line represents a bond via which the rest of the structure (IV) is connected to the nucleoside moiety (e.g. directly or via the Cgp' moiety), and R12, R13, and R14 are independently selected from aromatic ring moieties (aryl groups), each aromatic ring moiety comprising 4-, 5-, or 6-membered rings, provided that one of R12, R13, and R14 is substituted by being bonded (via the Cgp group) to the reactive phosphorus group. Each aromatic ring moiety can independently be heterocyclic, non-heterocyclic, polycyclic or part of a fused ring system. Each aromatic ring moiety can be unsubstituted or substituted with one or more groups each independently selected from the group consisting of lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxylthio, mercapto, amino, imino, halo, cyano, nitro, nitroso, azido, carboxy, sulfide, sulfone, sulfoxy, phosphoryl, silyl, silyloxy, and boronyl; provided that, as noted above, one of R12, R13, and R14 is substituted by being bound to the reactive phosphorus group, e.g. via the linking group Cgp, or further e.g. via a direct covalent bond between a member atom of the ring and the reactive phosphorus group.

Typical triaryl methyl groups that may be employed in embodiments herein are described in U.S. Pat. No. 4,668,777 to Caruthers, again provided that, as noted above, one of R12, R13, and R14 is substituted by being bound to the reactive phosphorus group; use of such triaryl methyl groups in accordance with the present invention is within ordinary skill in the art given the disclosure herein. A substituted triaryl methyl group may have one substituent (i.e. a singly substituted triaryl methyl group) on one of the aromatic rings of the triaryl methyl group, or may have multiple substituents (i.e. a multiply substituted triaryl methyl group) on one or more of the aromatic rings of the triaryl methyl group. As used herein, an aromatic ring moiety may be referenced as an "aromatic ring structure". As used herein, the "central methyl carbon" of a triaryl methyl group is the carbon bonded directly to the three aromatic ring structures.

In certain embodiments, R12 and R13 are each independently selected from substituted or unsubstituted aromatic groups such as phenyl, biphenyl, naphthanyl, indolyl, pyridinyl, pyrrolyl, thiophenyl, furanyl, annulenyl, quinolinyl, anthracenyl, and the like, and R14 is selected from substituted aromatic groups such as phenyl, biphenyl, naphthanyl, indolyl, pyridinyl, pyrrolyl, thiophenyl, furanyl, annulenyl, quinolinyl, anthracenyl, and the like. In some embodiments, at least one of R12, R13 and R14 is selected from substituted or unsubstituted aromatic groups other than phenyl such as naphthanyl, indolyl, pyridinyl, pyrrolyl, furanyl, annulenyl, quinolinyl, anthracenyl, and the like; in such embodiments zero, one, or two of R12, R13, and R14 are selected from substituted or unsubstituted phenyl, provided that, as noted above, one of R12, R13, and R14 is substituted by being bound to the reactive phosphorus group (e.g. through Cgp).

In some embodiments, R12, R13, and R14 are independently selected from structure (V).

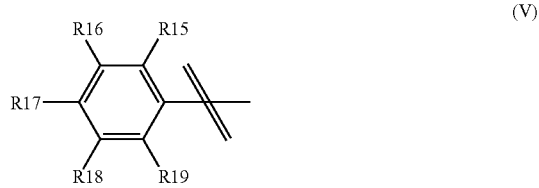

(V)

In structure (V), the broken line represents the bond to the central methyl carbon of the triaryl methyl linker group, and R15, R16, R17, R18, and R19 are each independently selected from hydrido, lower alkyl, aryl, aralkyl, lower alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl; and lower alkyl substituted with one or more groups selected from lower alkyl, alkoxy, thioalkyl, hydroxyl, thio, mercapto, amino, imino, halo, cyano, nitro, nitroso, azido, carboxy, sulfide, sulfone, sulfoxy, phosphoryl, silyl, silyloxy, and boronyl, provided that, for R14, one of the groups R15, R16, R17, R18, and R19 denotes the linkage to the reactive phosphorus group, or is the group via which the triaryl methyl linker group is attached to the reactive phosphorus group (e.g. through Cgp).

In particular embodiments, R12, R13, and R14 are each independently selected from phenyl, methoxyphenyl, dimethoxyphenyl, and trimethoxyphenyl groups, such that the Trl-group may be a trityl group, a monomethoxytrityl group, a dimethoxytrityl group, a trimethoxytrityl group, a tetramethoxytrityl group, a pentamethoxytrityl group, a hexamethoxytrityl group and so on; again provided as described above that one of R12, R13, and R14 is substituted by being bound to the reactive phosphorus group (e.g. through Cgp).

In particular embodiments, R12, R13, and R14 are each independently selected from phenyl, methoxyphenyl groups, dimethoxyphenyl groups, trimethoxyphenyl groups, tetramethoxyphenyl groups, pentamethoxyphenyl groups, or furyanyl groups such that the Trl-group may be a substituted trityl group, a monomethoxytrityl group, a dimethoxytrityl group, a trimethoxyl trityl group, a tetramethoxy trityl group, a pentamethoxytrityl group, an anisylphenylfuranylmethyl group, a dianisylfuranylmethyl group, a phenyldifuranylmethyl group, an anisyldifuranylmethyl group or a trifuranylmethyl group, again provided as described above that one of R12, R13, and R14 is substituted by being bound to the reactive phosphorus group (e.g. through Cgp).

Still referring to structure (I), the Cgp group is selected from (1) a linking group linking the reactive phosphorus group and the triaryl methyl linker group (typically Cgp is bound to a ring atom of one of the aryl groups of the triaryl methyl linker group, i.e. the Cgp group may be considered a substituent of one of the aryl groups of the triaryl methyl linker group); or (2) a covalent bond between the reactive phosphorus group and the triaryl methyl linker group (e.g. the reactive phosphorus group is bound to a ring atom of one of the aryl groups of the triaryl methyl linker group, i.e. the reactive phosphorus group may be considered a substituent of one of the aryl groups of the triaryl methyl linker group). In particular embodiments, the Cgp group may be any appropriate linking group (referenced herein as the Cgp linker group) that links the reactive phosphorus group and the triaryl methyl linker group, the Cgp linker group typically selected from (1) a lower alkyl group; (2) a modified lower alkyl group in which one or more linkages selected from ether-, oxo-, thio-, amino-, and phospho- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, oxo-, thio-, amino-, and phospho- is present. The Cgp linker group may be bonded to the adjacent triaryl methyl linker group at any position of the Cgp linker group available to bind to the adjacent triaryl methyl linker group. Similarly, the Cgp linker group may be bonded to the adjacent reactive phosphorus group at any position of the Cgp linker group available to bind to the adjacent reactive phosphorus group. In certain embodiments, the Cgp linker group is a single non-carbon atom, e.g. —O—, or a single non-carbon atom with one or more hydrogens attached, e.g. —N(H)—. In an embodiment, the Cgp linker group is selected from optionally substituted lower alkyl. In another embodiment, the Cgp linker group is selected from optionally substituted ethoxy, propoxy, or butoxy groups.

Again referring to structure (I), the Cgp' group is selected from (1) a linking group linking the central methyl carbon of the triaryl methyl linker group to the nucleoside moiety (typically at the 5'-O or 3'-O of the nucleoside moiety, or other suitable site of the nucleoside moiety); or (2) a covalent bond between the central methyl carbon of the triaryl methyl linker group and the nucleoside moiety (e.g. at the 5'-O or 3'-O of the nucleoside moiety, or other suitable site of the nucleoside moiety). In particular embodiments, the Cgp' group may be any appropriate linking group (referenced herein as the Cgp' linker group) that links the triaryl methyl linker group to the nucleoside moiety, the Cgp' linker group typically selected from (1) a lower alkyl group; (2) a modified lower alkyl group in which one or more linkages selected from ether-, oxo-, thio-, amino-, and phospho- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, oxo-, thio-, amino-, and phospho- is present. The Cgp' linker group may be bonded to the adjacent triaryl methyl linker group at any position of the Cgp' linker group available to bind to the adjacent triaryl methyl linker group. Similarly, the Cgp' linker group may be bonded to the adjacent nucleoside moiety at any position of the Cgp' linker group available to bind to the adjacent nucleoside moiety. In certain embodiments, the Cgp' linker group is a single non-carbon atom, e.g. —O—, or a single non-carbon atom with one or more hydrogens attached, e.g. —N(H)—. In an embodiment, the Cgp' linker group is selected from optionally substituted lower alkyl. In another embodiment, the Cgp' linker group is selected from optionally substituted ethoxy, propoxy, or butoxy groups.

In particular embodiments, the Cgp' linker group comprises a polynucleotide moiety, typically having 1 to about 200 nucleotide subunits, more typically 1 to about 60 nucleotide subunits, still more typically in the range from 1 to about 20 nucleotide subunits. In certain embodiments, the polynucleotide moiety has 1, 2, 3, 4, or 5 nucleotide subunits. The polynucleotide moiety may have appropriate protecting groups as are known in the art of polynucleotide synthesis to prevent or reduce undesired chemical reactivity. The polynucleotide moiety typically includes naturally occurring and/or non-naturally occurring heterocyclic bases and may include heterocyclic bases which have been modified, e.g. by inclusion of protecting groups or any other modifications described herein, or the like. As used herein, "polynucleotide moiety" references a series of connected nucleotide subunits that is a portion of a larger molecule. The polynucleotide moiety is typically bound to the triaryl methyl linker group of structure (I) via a 3' —O— or a 5' —O— of the polynucleotide moiety, although any other suitable site is contemplated and is within the scope of the invention. The polynucleotide moiety is typically bound to the sugar group of the nucleoside moiety (described below) via a 3' —O— or a 5' —O— of the polynucleotide moiety, although other sites of the polynucleotide moiety may be bound to the sugar group of the nucleoside moiety: such other sites are contemplated and are within the scope of the invention.

Again referring to structure (I), the Nucl group is a nucleoside moiety having a sugar group attached to a heterocyclic base. The sugar group of the nucleoside moiety may be any sugar group known in the art of polynucleotides and polynucleotide analogues. The sugar group is bound to the reactive phosphorus group via the triaryl methyl linker group, and also via the intervening Cgp and Cgp' groups in the embodiments depicted by structure (I). The sugar group typically includes a hydroxyl protecting group. In use, the hydroxylprotecting group protects a hydroxyl group (typically the 5'-OH or the 3'-OH) of the sugar which is later deprotected to serve as the site for attachment of nucleotide monomers during typical polynucleotide synthesis.

The sugar group may be any sugar group (or substituted sugar group) known in the art of nucleotide synthesis and nucleotide analog synthesis. Representative sugar groups may be selected from monosaccharides, ketoses, aldoses, pentoses (five carbon sugars), hexoses (six carbon sugars), including any such groups modified by e.g. oxidation, deoxygenation, introduction of other substituents, alkylation and acylation of hydroxyl groups, and chain branching. The sugar group is typically ribose or 2'-deoxyribose, although other sugars may be used. In an embodiment, the sugar is arabinose. In another embodiment, the sugar is selected from xylose or lyxose. In typical embodiments, the sugar group is a monosaccharide; representative monosaccharides include glycerose, dihydroxyacetone, erythrose, erythrulose, xylose, lyxose, arabinose, ribose, xylulose, ribulose, rhamnose, fucose, glucose, mannose, galactose, fructose, sorbose, glucoheptose, galamannoheptose, sedoheptulose, mannoheptulose, and others.

In certain embodiments, the sugar group is a polyhydroxyketone having the structure (IIIa)

H—[CH(OH)]$_n$—C(=O)—[CH(OH)]$_m$—H    (IIIa)

in which n is an integer from 1 to about 5 and m is an integer from 1 to about 5; provided that one of the hydrogens or hydroxyls in structure (IIIa) is replaced by the Cgp' group; and provided that the heterocyclic base is directly bound to one of the carbons of structure (IIIa) (thereby replacing a hydrogen or hydroxyl of structure (IIIa) or adding to the carbonyl carbon of structure (IIIa)). It will be readily apparent to the reader skilled in the art that, in embodiments in which the heterocyclic base is added to (i.e. bound directly to) the carbonyl carbon of structure (IIIa), the other groups (e.g. the carbonyl oxygen) bound to the carbonyl carbon may be changed to preserve normal valency rules for the groups, e.g. to hydroxyl, hydrido, or other suitable groups. Typically, the polyhydroxyketone has at least three carbon atoms, typically at least four carbon atoms, more typically at least five carbon atoms, and typically has up to about eight carbon atoms, more typically up to about ten carbon atoms. In particular embodiments, the sugar group is based on the given structure in this paragraph but is modified, e.g. by deoxygenation, by introduction of other substituents (e.g. replacement of a hydrogen or hydroxyl by a substituent), by alkylation and/or acylation of hydroxyl groups, by chain branching, and by formation of an intramolecular hemiacetal, and by combinations of the above. Also contemplated are sugar groups in which the given structure (IIIa) is modified by intramolecular cyclization reaction, e.g. forming a furanose, pyranose, or other ring structure. As used herein, a sugar group "based on" structure (IIIa) references any structure disclosed in this paragraph, also encompassing the modifications to structure (IIIa) as described in this paragraph.

In certain embodiments, the sugar group is a polyhydroxyaldehyde having the structure (IIIb)

H—[CH(OH)]$_n$—C(=O)H    (IIIb)

in which n is an integer from 2 to about 8, typically from 3 to 7, more typically from 4 to 6; provided that one of the hydrogens or hydroxyls in structure (IIIb) is replaced by the Cgp' group; and provided that the heterocyclic base is directly bound to one of the carbons of structure (IIIb) (thereby replacing a hydrogen or hydroxyl of structure (IIIb) or adding to the carbonyl carbon of structure (IIIb)). It will be readily apparent to the reader skilled in the art that, in embodiments in which the heterocyclic base is added to (i.e. bound directly to) the carbonyl carbon of structure (IIIb), the other groups (e.g. the carbonyl oxygen, the aldehydic hydrogen) bound to the carbonyl carbon may be changed to preserve normal valency rules for the groups, e.g. to hydroxyl, hydrido, or other suitable groups. In particular embodiments, the sugar group is based on the given structure in this paragraph but is modified, e.g. by deoxygenation, by introduction of other substituents (e.g. replacement of a hydrogen or hydroxyl by a substituent), by alkylation and/or acylation of hydroxyl groups, by chain branching, and by formation of an intramolecular hemiacetal, and by combinations of the above. Also contemplated are sugar groups in which the given structure (IIIb) is modified by intramolecular cyclization reaction, e.g. forming a furanose, pyranose, or other ring structure. As used herein, a sugar group "based on" structure (IIIb) references any structure disclosed in this paragraph, also encompassing the modifications to structure (IIIb) as described in this paragraph.

The sugar group of the nucleoside moiety typically has one or more substituents, e.g. the Cgp' group (including other groups attached thereto, as described herein), further e.g. one or more hydroxyl protecting groups. Typically, a hydroxylprotecting group will be blocking a reactive site hydroxyl group of the sugar group, wherein the hydroxyl protecting group is intended to be removed prior to use of the functionalized substrate for polynucleotide synthesis. The reactive site hydroxyl is typically the 3' hydroxyl group or the 5' hydroxyl group of the nucleoside moiety, although other sites may serve as the reactive site hydroxyl (depending in the identity of the sugar group).

In certain embodiments, the hydroxylprotecting group on the sugar group is any protecting group that is known to be releasable under conditions of simultaneous deprotection and oxidation during the polynucleotide synthesis cycle. Exemplary protecting groups that may be released to free the hydroxyl group during the simultaneous deprotection and oxidation step are described in U.S. Pat. No. 6,222,030 to Dellinger et al.; U.S. Pat. Appl'n Publ'n No. US2002/0058802 A1 to Dellinger et al., now U.S. Pat. No. 7,135,565; and Seio et al. (2001) Tetrahedron Lett. 42 (49):8657-8660. In certain embodiments, the protecting groups may be carbonate protecting groups as described in U.S. Pat. No. 6,222,030. In some embodiments, the protecting groups may be aryl carbonate protecting groups as described in U.S. Pat. No. 6,222,030. In other embodiments, the protecting groups may be non-carbonate protecting groups as described in U.S. Pat. Appl'n Publ'n No. US2002/0058802 A1, now U.S. Pat. No. 7,135,565; such as for example, 3'- or 5'-O-silyl or -siloxyl protecting groups, 3'- or 5'-O-ester protecting groups, and 3'- or 5'-O-carbamate protecting groups. The hydroxylprotecting group may be, for example, a protecting group which is labile under nucleophilic attack under neutral or mildly basic conditions. Examples of protecting groups which are labile under nucleophilic attack under neutral or mildly basic conditions are: ester protecting groups, carbamate protecting groups, siloxane protecting groups, silane protecting groups, and sulfonate protecting groups that β-eliminate. Examples of suitable hydroxylprotecting groups are described in "Protective Groups in Organic Synthesis" by T. W. Green, Wiley Interscience.

As described above with regard to structure (I), the Nucl group is a nucleoside moiety having a sugar group bound to a heterocyclic base. The heterocyclic base of the nucleoside moiety may be selected from the naturally occurring purine and pyrimidine bases, e.g., adenine (A), thymine (T), cytosine (C), guanine (G), or uracil (U), or modified purine and pyrimidine bases and other heterocyclic bases which have been modified, and common analogs, e.g. such as are recited herein. Certain nucleotide analogs that are contemplated in this context include those described in U.S. Pat. Appl'n Ser. No. 10/324,409 entitled "Method Of Producing Nucleic Acid Molecules With Reduced Secondary Structure", filed on Dec. 18, 2002, now U.S. Pat. No. 6,908,164; and also those described in U.S. Pat. Appl'n Ser. No. 09/358,141 entitled "Method Of Producing Nucleic Acid Molecules With Reduced Secondary Structure", filed on Jul. 20, 1999now abandoned. In particular embodiments, the heterocyclic base may have a protecting group, as is commonly known in the art of polynucleotide synthesis.

The heterocyclic base is typically bound by an N-glycosidic linkage to the 1' carbon of the sugar group, although other configurations are to be encompassed by the invention. In other embodiments, the heterocyclic base is bound by a C-glycosidic linkage to the 1' carbon of the sugar group. In some embodiments the heterocyclic base is bound to a carbon other than the 1' carbon of the sugar group. Other positions of the heterocyclic base (the atom of the heterocyclic base ring via which the heterocyclic base is linked to the sugar group) and other linkages between the heterocyclic base and the sugar group may be practiced by those of ordinary skill in the synthesis of nucleotide analogs given the disclosure herein, especially where analogous structures having the given heterocyclic base and sugar group are known in the art.

The nucleoside moiety is typically bound to the triaryl methyl linker group via a 3' —O— or a 5' —O— of the nucleoside moiety (also via the Cgp' linker group, if present), although other sites of the nucleoside moiety are contemplated and are within the scope of the invention. Use of such other sites of the nucleoside moiety by which the nucleoside moiety may be bound to the triaryl methyl linker group are within the skill in the art given the disclosure herein.

In typical embodiments, a reagent provided in accordance with the present invention has the structure (VII)

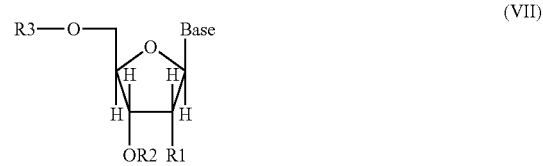

(VII)

Wherein the groups are defined as follows:

O and H represent oxygen and hydrogen, respectively

Base is a heterocyclic base.

R1 is typically hydrido or hydroxyl (or hydroxylprotecting group), wherein when R1 is hydrido, the sugar is 2'-deoxyribose, as will be present in DNA synthesis, and when R1 is hydroxyl (or hydroxylprotecting group), the sugar is ribose, as will be present in RNA synthesis. In certain embodiments, R1 is lower alkyl, modified lower alkyl, or alkoxy.

One of R2 or R3 is Phos-Cgp-Trl-Cgp'- as referenced above with regard to structure (I), and the other of R2 or R3 is a hydroxylprotecting group as further described above with respect to the hydroxylprotecting group on the sugar group of the nucleoside moiety of structure (I). In some embodiments, the hydroxylprotecting group is a protecting group which is labile under nucleophilic attack under neutral or mildly basic conditions.

With regard to the description of R2 and R3 of structure (VII), it is well known within the art that synthesis of a polynucleotide may typically be performed in a 3' to 5' direction, or, alternatively, in the 5' to 3' direction. It will be apparent from the description herein given ordinary knowledge in the art that the reagents and functionalized supports provided in accordance with the present invention may comprise nucleoside moieties bound to the triaryl methyl linker group in different orientations in different embodiments, e.g. the hydroxylprotecting group and Phos-Cgp-Trl-Cgp'- designated by R2 and R3 may occupy either the 5'-O or 3'-O positions as described above. The synthesis and use of such alternate embodiments will be readily apparent given the skill in the art and the disclosure herein.

The present invention further provides methods of making functionalized supports for polynucleotide synthesis using reagents having the structure (I) as described herein. In the method, a solid support, to which an available reactive group is bound, is contacted with a reagent having the structure (I)

under conditions and for a time sufficient to result in a nucleoside moiety bound to the support via a triaryl methyl linker group. The product of the method typically has the structure (II)

as described in further detail, below.

The solid support should be essentially inert to the conditions of reactions used for polynucleotide synthesis. Typically the solid support includes a solid substrate having a surface to which the available reactive group is bound. The solid substrate typically comprises a material that is stable to conditions used in the synthesis of polynucleotides; such materials include, but are not limited to, support materials that are typically used for solid-phase chemical synthesis, e.g. cross-linked polymeric materials (e.g. divinylbenzene styrene-based polymers), agarose (e.g. SEPHAROSE media), dextran (e.g. SEPHADEX media), cellulosic polymers, polyacrylamides, silica, glass (such as controlled pore glass "CPG"), ceramics, and the like.

In certain embodiments, the solid support comprises a solid substrate and a modification layer disposed on (or bound to, e.g. directly or indirectly) the substrate, and the available reactive group is bound to (e.g. directly or indirectly) the modification layer. Such modification layer may be formed on the substrate by methods known in the art of modifying surface properties of supports used in polynucleotide synthesis, or known in the art of modifying supports to provide desired surface properties. In certain embodiments, the modification layer may be, e.g. a coating, a material deposited by deposition techniques known in the art, a hydrophobic layer, or a hydrophilic layer. In particular embodiments, the modification layer comprises a silane group, to which the available reactive group is bound, directly or indirectly, e.g. via any linking group effective to link the available reactive group to the silane group and stable to the conditions used in polynucleotide synthesis. Particularly contemplated are supports taught in U.S. Pat. No. 6,258,454 to Lefkowitz et al. (2001), which describes a moiety bound to a substrate via a linking group attached to a silane group bound to the substrate.

Functionalized supports in accordance with the present invention may be made using silane modified substrates such as are employed in the Lefkowitz '454 patent and modifications thereof. In such methods, an available reactive group attached (directly or indirectly, e.g. via a linking group) to the silane group on the substrate provides a site for further attachment to the substrate to occur. The substrate bearing the available reactive group is then contacted with a reagent having a reactive phosphorus group, the reagent further having a triaryl methyl linker group bound to the reactive phosphorus group. The reactive phosphorus group is capable of reacting with the available reactive group attached to the substrate to result in attachment of the triaryl methyl linker group to the solid support. Of course, other moieties, such as a nucleoside moiety, attached to the triaryl methyl linker group will thusly also be attached to the solid support. The resulting functionalized support may be used in polynucleotide synthesis. The available reactive group attached to the substrate will typically be selected from amine, hydroxyl, sulfhydryl, carboxyl, carbonyl, phosphate and thiophosphate, and combinations thereof; more typically the available reactive group will be selected from amine, hydroxyl, and sulfhydryl, and combinations thereof. The reactive phosphorus group is chemically reactive with (and forms a covalent bond with) the available reactive group attached to the substrate. In certain embodiments, the reactive phosphorus group is a phosphoramidite. Selection of an appropriate reactive phosphorus group will be based on the identity of the available reactive group attached to the substrate, and vice versa. Such selection is within the skill of those in the art given the disclosure herein.

An available reactive group bound to the solid support is typically employed in methods of making a functionalized support. The available reactive group bound to the solid support may be any suitable group capable of reacting with the reactive phosphorus group to result in the nucleoside moiety being bound to the solid support via a triaryl methyl linker group, wherein the triaryl methyl linker group is bound to the solid support via a phosphorus-containing linkage group. The available reactive group bound to the solid support typically is selected from hydroxyl, thio and amino, although any other group effective to react with the reactive phosphorus group to produce a phosphorus-containing linkage group may be the available active group. In particular embodiments, the available reactive group is hydroxyl.

Upon contacting a reagent having the structure (I), which has a reactive phosphorus group, with an available reactive group bound to the solid support, reaction of the reactive phosphorus group with the available reactive group results in the formation of a phosphorus-containing linkage group, via which the triaryl methyl linker group is attached to the solid support. Initially, the phosphorus-containing linkage typically comprises a phosphite group, such as a phosphite ester.

In particular embodiments, the product of the above-described contacting step is then contacted with an oxidizing agent and/or a deprotecting agent. In certain embodiments, the product is contacted with a combined deprotection/oxidation agent, i.e. the deprotection and oxidation are performed concurrently. The deprotection agent serves to remove a hydroxylprotecting group from the product, thereby providing an available hydroxyl for polynucleotide synthesis. The oxidation agent serves to oxidize the phosphorus-containing linkage, for example from phosphite to phosphate or from phosphite ester to phosphate ester.

The deprotection/oxidation reaction essentially may be conducted under the reported conditions used for the synthesis of polynucleotides as described in, e.g. U.S. Pat. No. 6,222,030 to Dellinger et al.; U.S. Pat. Appl'n Publ'n No. US2002/0058802 A1 to Dellinger et al., now U.S. Pat. No. 7,135,565; Seio et al. (2001) Tetrahedron Lett. 42 (49):8657-8660. As will be appreciated by those of ordinary skill in the art given the disclosure herein, the conditions for the deprotection/oxidation step may vary depending on the nature of the protecting groups used. In order to be compatible with the triaryl methyl linker group provided for by the current invention, the conditions for the simultaneous deprotection and oxidation reaction (i.e. required conditions for release of the hydroxyl protecting group and the oxidation of the phosphorus-containing linkage) should be selected such that the nucleoside moiety remains attached to the solid support via the triaryl methyl linker group. Typical conditions for the deprotection/oxidation reaction include a pH in the neutral to moderately basic range. In particular embodiments, the pH of the deprotection/oxidation reaction is at least about 6.0, typically at least about 6.5, more typically at least about 7.0, still more typically at least about 7.5, and the pH is typically less than about 12, typically less than about 11, more typically less than about 10.5, still more typically less than about 10.

The combined deprotection/oxidation agent may be selected to provide desired synthesis conditions and characteristics, as are described herein. In an embodiment, the combined deprotection/oxidation agent provides for contacting the functionalized support with an alpha effect nucleophile under neutral or mildly basic aqueous conditions to remove reactive site hydroxylprotecting groups where such protecting groups are labile under nucleophilic attack; the alpha effect nucleophile also serves to oxidize the phosphite triester linkage to a phosphotriester linkage.

The deprotection/oxidation agent may be any compound or mixture of compounds that is compatible with the functionalized substrate and has the properties discussed herein. Typically, the deprotection/oxidation agent includes a concentration of an oxidant that is high enough to rapidly oxidize the newly formed phosphite linkage. This is typically at least 0.1% vol/vol, typically at least 0.5% vol/vol, more typically at least about 1.0% vol/vol, still more typically at least about 3.0% vol/vol. The concentration of the oxidant typically should be low enough to avoid appreciable (e.g. less than 5%) amounts of oxidative destruction of the nucleoside moiety. This concentration is typically less than 10% vol/vol, more typically less than 9% vol/vol, still more typically less than 7% vol/vol.

The deprotection/oxidation agent in typical embodiments provides a source of a peroxyanion at neutral to mildly basic pH in the reaction mixture during the deprotection/oxidation reaction. The concentration of the peroxyanion will be related to the acid dissociation constant of the hydroperoxide species at equilibrium. The concentration of peroxyanion is typically in the range 0.01% to 99% of the total hydroperoxide concentration (i.e. sum of all hydroperoxide species, e.g. protonated and unprotonated forms), more typically in the range 0.05% to 90% of the total hydroperoxide concentration, yet more typically in the range 0.1% to 50% of the total hydroperoxide concentration, still more typically in a range of 1.0% to 30% of the total hydroperoxide concentration.

In certain embodiments, the alpha effect nucleophile is a peroxide or a mixture of peroxides. In typical embodiments, the pH at which the deprotection/oxidation reaction is conducted is generally in the range of about three pH units below the pKa of the alpha effect nucleophile (e.g. the pKa for formation of the corresponding peroxy anion) up to about three pH units above the pKa of the alpha effect nucleophile. More typically, the pH of the deprotection/oxidation reaction is in the range of about one pH unit below the pKa of the alpha effect nucleophile up to about pH 11. In certain embodiments, the pH will be the range from about the pKa of the peroxide up to a pH of about 11. The peroxide may be either inorganic or organic. Suitable inorganic peroxides include those of the formula M+OOH—, where M+ is any counter ion, including for example H+, Li+, Na+, K+, Rb+, Cs+, or the like; and lithium peroxide or hydrogen peroxide and alkaline stabilized forms thereof can be particularly suitable. Suitable organic peroxides include those of the formula ROOH, where R is selected from the group consisting of alkyl, aryl, substituted alkyl, substituted aryl, and modified alkyl. More particularly, the organic peroxide will have one of the following three general structures (VII), (IX) or (X).

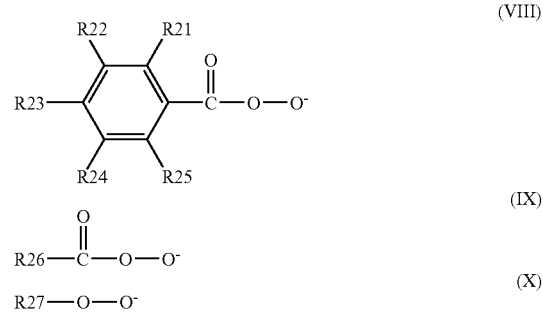

in which R21 through R27 are generally hydrocarbyl optionally substituted with one or more nonhydrocarbyl substituents and optionally containing one or more nonhydrocarbyl linkages. Generally, R21 through R27 are independently selected from the group consisting of hydrido, alkyl, modified alkyl, aryl, aralkyl, cycloalkyl, cycloalkylalkyl, alkenyl, cycloalkenyl, alkynyl aralkynyl, cycloalkynyl, substituted aralkyl, substituted cycloalkyl, substituted cycloalkylalkyl, substituted alkenyl, substituted cycloalkenyl, substituted alkynyl substituted aralkynyl, substituted cycloalkynyl, hydrocarbyl, and substituted hydrocarbyl. T-butyl-hydroperoxide or metachloroperoxybenzoic acid can be particularly suitable. As a specific example, the m-chloroperoxybenzoic acid (mCPBA) peroxy anion has been found to be useful for removal of protecting groups on the reactive site hydroxyl.

A functionalized support in accordance with the invention comprises a nucleoside moiety attached to a solid support via a triaryl methyl linker group, wherein the triaryl methyl linker group is attached to the solid support via a phosphorus-containing linkage group, e.g. a phosphite group, further e.g. a phosphate group. As used herein, the term phosphite group includes phosphite ester groups, and the term phosphate group includes phosphate ester groups.

A functionalized support having a cleavable linker group produced in accordance with the present invention typically has the structure (II)

Wherein the groups are defined as follows:

◯- is a solid support, essentially as described above with respect to the methods of making functionalized supports in accordance with the invention.

Trl, Cgp', and Nucl are as defined above.

Plg is a phosphorus-containing linkage group, e.g. a phosphite group or a phosphate group. The phosphorus-containing linkage group may be any linkage group that may result from the reaction of an available reactive group with a reactive phosphorus group. Typical phosphorus-containing linkage groups include, e.g. a phosphite group, further e.g. a phosphate group.

Cgp" is a linking group linking the phosphorus-containing linkage group and the triaryl methyl linker group, or is a bond linking the phosphorus-containing linkage group and the triaryl methyl linker group.

The Cgp" group is selected from (1) a linking group linking the phosphorus-containing linkage group and the triaryl methyl linker group (typically Cgp" is bound to a ring atom of one of the aryl groups of the triaryl methyl linker group, i.e. the Cgp group may be considered a substituent of one of the aryl groups of the triaryl methyl linker group); or (2) a covalent bond between the phosphorus-containing linkage group and the triaryl methyl linker group (e.g. the phosphorus-containing linkage group is bound to a ring atom of one of the aryl groups of the triaryl methyl linker group, i.e. the phosphorus-containing linkage group may be considered a substituent of one of the aryl groups of the triaryl methyl linker group). In particular embodiments, the Cgp" group may be any appropriate linking group (referenced herein as the Cgp" linker group) that links the phosphorus-containing linkage group and the triaryl methyl linker group, the Cgp" linker group typically selected from (1) a lower alkyl group; (2) a modified lower alkyl group in which one or more linkages selected from ether-, oxo-, thio-, amino-, and phospho- is present; (3) a modified lower alkyl substituted with one or more groups including lower alkyl; aryl, aralkyl, alkoxyl, thioalkyl, hydroxyl, amino, sulfonyl, halo; or (4) a modified lower alkyl substituted with one or more groups including lower alkyl; alkoxyl, thioalkyl, hydroxyl, amino, sulfonyl, halo, and in which one or more linkages selected from ether-, oxo-, thio-, amino-, and phospho- is present. The Cgp" linker group may be bonded to the adjacent triaryl methyl linker group at any position of the Cgp" linker group available to bind to the adjacent triaryl methyl linker group. Similarly, the Cgp" linker group may be bonded to the adjacent phosphorus-containing linkage group at any position of the Cgp" linker group available to bind to the adjacent phosphorus-containing linkage group. In certain embodiments, the Cgp" linker group is a single non-carbon atom, e.g. —O—, or a single non-carbon atom with one or more hydrogens attached, e.g. —N(H)—. In an embodiment, the Cgp" linker group is selected from optionally substituted lower alkyl. In another embodiment, the Cgp" linker group is selected from optionally substituted ethoxy, propoxy, or butoxy groups.

In certain embodiments, a functionalized support provided in accordance with the current invention has the structure (XI)

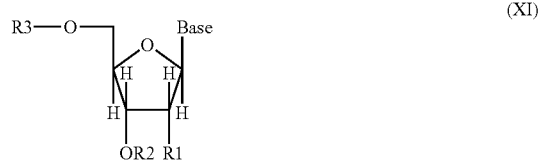

(XI)

Wherein the groups are defined as follows:
O and H represent oxygen and hydrogen, respectively.
Base is a heterocyclic base, as described herein.
R1 is typically hydrido or hydroxyl (or hydroxylprotecting group), wherein when R1 is hydrido, the sugar is 2'-deoxyribose, as will be present in DNA synthesis, and when R1 is hydroxyl (or hydroxylprotecting group), the sugar is ribose, as will be present in RNA synthesis. In certain embodiments, R1 is lower alkyl, modified lower alkyl, or alkoxy.

One of R2 or R3 is a hydroxylprotecting group or a hydrido; and the other of R2 or R3 is O-Plg-Cgp"-Trl-Cgp'—as referenced above with regard to structure (II).

Figure 2:
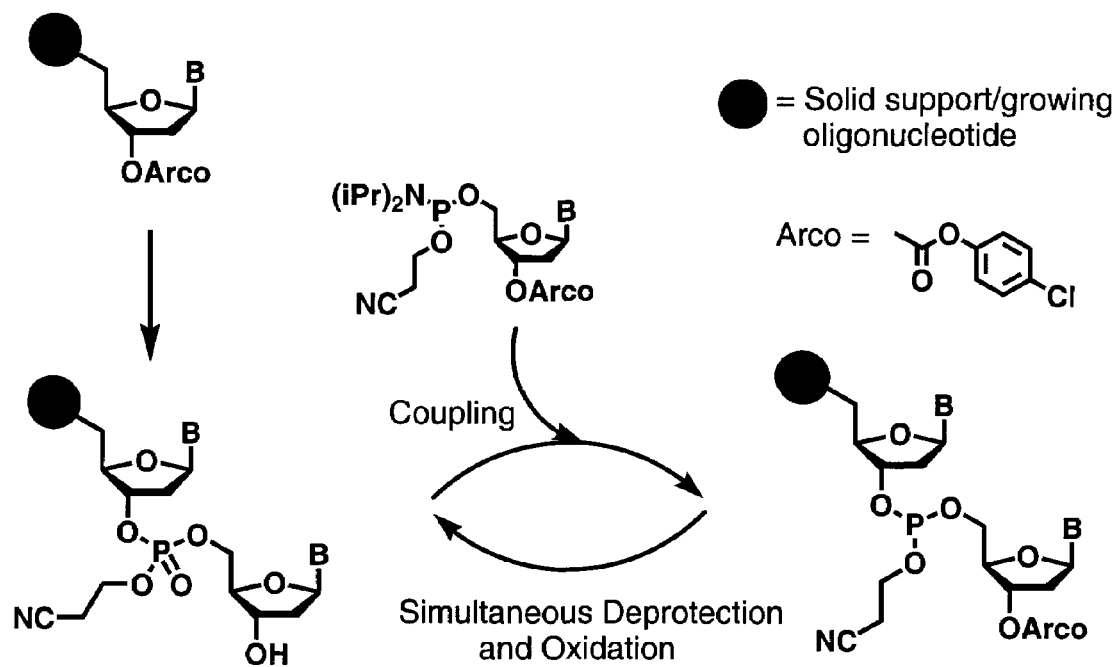
FIG. 2 depicts a synthesis scheme employing a two step synthesis cycle, including a coupling step and a simultaneous deprotection and oxidation step.

A functionalized support in accordance with the present invention may then be used to perform polynucleotide synthesis. In a method for synthesis of a polynucleotide, the functionalized support is contacted with a precursor (typically a hydroxyl-protected activated nucleoside monomer) under conditions and for a time sufficient to allow the precursor to react with an available reactive site hydroxyl group of the nucleoside moiety. Such reactions may be repeated a plurality of times to result in the synthesized polynucleotide bound to the surface via a triaryl methyl linker group. Such reactions and typical precursors used in such reactions are described in, e.g. U.S. Pat. No. 6,222,030 to Dellinger et al.; U.S. Pat. Appl'n Publ'n No. US2002/0058802 A1 to Dellinger et al., now U.S. Pat. No. 7,135,565; Seio et al. (2001) Tetrahedron Lett. 42 (49):8657-8660; and in the applications for patents by Dellinger et al. co-filed with the present application (referenced above). These references describe two-step methods of (1) coupling a precursor to a growing oligonucleotide chain, and (2) deprotecting the product using an alpha effect nucleophilic reagent that also oxidizes the internucleotide linkage to give a phosphotriester bond. The coupling and deprotection/oxidation steps are repeated as necessary to give a polynucleotide having a desired sequence and length. FIG. 2 shows a synthesis scheme for 5' to 3' polynucleotide synthesis such as is taught in the references cited in this paragraph. As may be seen in the synthesis scheme set out in FIG. 2, in the second step of the synthesis cycle, deprotection and oxidation occur concurrently. The synthesis scheme illustrated in FIG. 2 may be contrasted with that schematically illustrated in FIG. 1, in which the synthesis scheme entails separate oxidation and deprotection steps and occurs in the 3' to 5' direction.

The invention thus further provides a method for synthesizing a polynucleotide on a functionalized support, wherein the functionalized support has a surface to which a nucleoside moiety is bound via an intermediate moiety or moieties including a triaryl methyl linker group and optional linking groups (e.g. Cgp", Cgp'). The nucleoside moiety, which has the reactive site hydroxyl, is accessible to participate in polynucleotide synthesis reaction as described. In an embodiment, the method comprises forming an internucleotide bond by contacting a functionalized support having the structure (II) with a precursor (typically a hydroxyl-protected activated nucleoside monomer) as described above under conditions and for a time sufficient to allow the precursor to react with the nucleoside moiety of the functionalized support to result in formation of the internucleotide bond. In particular embodiments, the method comprises forming an internucleotide bond by contacting a functionalized support having the structure (XI) with a precursor as described above under conditions and for a time sufficient to allow the precursor to react with the nucleoside moiety of the functionalized support to result in formation of the internucleotide bond. In an embodiment, the method of synthesizing polynucleotides further includes, after the internucleotide bond is formed, exposing the result of the forming an internucleotide bond step to a composition which concurrently oxidizes the internucleotide bond and removes a hydroxylprotecting group (the simultaneous deprotection and oxidation step).

The use of a triaryl methyl linker group provides for release of the synthesized polynucleotide from the solid support. In typical embodiments, the synthesized polynucleotide may be released from the solid support to yield the polynucleotide free in solution (not attached to the support). This reaction typically is conducted under mildly acidic conditions. In particular embodiments, the synthesized polynucleotide is cleaved from the triaryl methyl linker group by weak acids under conditions that do not result in destruction of the glycosidic linkage, typically glacial acetic acid or glacial acetic acid/water mixtures.

EXAMPLES

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to perform the methods and use the compositions disclosed and claimed herein. Efforts have been made to ensure accuracy with respect to numbers (e.g., amounts, temperature, etc.) but some errors and deviations should be accounted for. Unless indicated otherwise, parts are parts by weight, percents are wt./wt., temperature is in ° C. and pressure is at or near atmospheric. Standard temperature and pressure are defined as 20° C. and 1 atmosphere.

A synthesis of reagents used in certain embodiments of the present invention is now described. It will be readily apparent that the reactions described herein may be altered, e.g. by using modified starting materials to provide correspondingly modified products, and that such alteration is within ordinary skill in the art. Given the disclosure herein, one of ordinary skill will be able to practice variations that are encompassed by the description herein without undue experimentation.

Abbreviations used in the examples include: THF is tetrahydrofuran; TLC is thin layer chromatography; HEX is hexane; $Et_3N$ is triethylamine; MW is molecular weight; AcCN is acetonitrile; sat'd is saturated; EtOH is ethanol; B is a heterocyclic base having an exocyclic amine group, $B^{Prot}$ is a heterocyclic base having an exocyclic amine group with a trityl protecting group on the exocyclic amine group; TiPSCl is 1,3-dichloro-1,1,3,3-tetraisopropyldisiloxane; TEMED is N,N,N',N'-Tetramethylethylenediamine; Py is pyridine; MeCN is acetonitrile; DMT is dimethoxytrityl; MMT is monomethoxytrityl; TMT is trimethoxytrityl; Cyt-$^{DMT}$ is cytosine which has a dimethoxytrityl protecting group on the exocyclic amine group; $Cyt^{TMT}$ is cytosine which has a trimethoxytrityl protecting group on the exocyclic amine group (and so on for other bases and protecting groups on the exocyclic amine group of the indicated base); MS is mass spectrometry, MS (ES) is mass spectrometry (electrospray), HRMS (FAB) is high resolution mass spectrometry (fast atom bombardment); DCM is methylene chloride; EtOAc is ethyl acetate; $^iPr$ is isopropyl; $Et_3N$ is triethylamine; TCA is trichloroacetic acid; TEAB is tetraethylammonium bicarbonate.

4-Hydroxy-4'-Methoxytrityl Alchol

Step 1

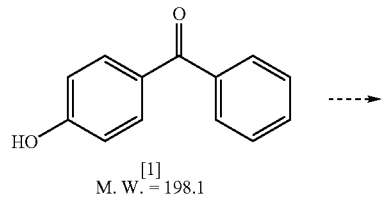

A. 25.0 g (126.2 mmoles) 4-hydroxy Benzophenone (1); Aldrich # H2020-2
B. 500 ml THF; Aldrich # 49446-1
C. 700 ml of a 0.5 M Solution in THF (175 mmoles) 4-Anisyl Magnesium Bromide; Alpha-Aesar # 89435

TLC System: HEX/EtOAc/Acetone (4:1:1)+0.5% $Et_3N$ on silica gel

Using a 3-L 3-neck round bottom flask with a mechanical stirrer, U-tube thermometer and drying tube, (A) was added to (B) and the solution was cooled to 4° C. in a dry-ice/acetone bath, under Argon atmosphere. (C) was added drop wise over a period of 1 hour. Precipitate forms tan pink color. The temperature was kept between 0-5° C. during the addition. The mixture was removed from the bath and stirred at ambient temperature (under Argon atmosphere) for 16-hours. The solvent was evaporated in vacuo. The residue was suspended in 300 ml ether and 200 mL cold water. The ether layer was extracted with 150 mL saturated $NaHCO_3$ and 150 mL saturated NaCl and dried with $MgSO_4$. The solvent was evaporated, and 66 g of an oily residue was obtained. The residue was dissolved in 50 mL DCM, 30 g silica gel added and column purified over silica gel, with DCM/AcCN (19:1) as the initial mobile phase, changing to DCM/AcCN (9:1) as mobile phase for elution of the product. The product was column purified a second time over silica gel using EtOAc/HEX (1:1) as mobile phase for elution of the product.

Theoretical Yield: 38.6 g

Actual Yield: 23.9 g [62%]

$^1$H NMR (CDCl$_3$) 3.78 (3H, s), 6.75 (2H, d, J=8.8), 6.83 (2H, d, J=8.8), 7.11 (2H, d, J=8.8), 7.17 (2H, d, J=8.8), 7.25-7.32 (5H, m); MS (ESI−) m/z 305 (M−1, 100); (ESI+) m/z 635 (M$_2$+Na, 33), 289 (M−H$_2$O, 100)

4-((3-Propoxy)-tert-Butyldimethylsilane)-4'-Methoxytrityl Alcohol

Step 2

TLC System: DCM/AcCN [19:1]

A. 24.0 g (78.0 mmoles) [2]

B. 21.6 g (156 mmoles) potassium carbonate MW=138.1; Aldrich # 20961-9

C. 60 g (235 mmoles) (3-Bromopropoxy)-tert-butyldimethylsilane MW=253.3; Aldrich # 42,906-6

D. Single (Dry) Crystal Potassium Iodide MN 166.1; Aldrich # 22194-5

E. 600 mL Toluene

Using a 2 L 3-neck round bottom flask equipped with a thermometer, reflux condenser, drying tube and stir bar, (A), (B) (C), and (D) were added to (E) in sequential order. The mixture was heated to reflux for 24 hours. The solvent was evaporated. The residue was partitioned between 750 mL DCM and 300 mL water. The DCM layer was washed twice with 400 mL sat'd NaCl then dried over $MgSO_4$.

Theoretical Yield: 37.3 g

Actual Yield: 16 g [43%]

MS (FAB+) m/z 479, 462 (M—OH, 100)

4-((3-Propoxy)-tert-Butyldimethylsilane)-4'-Methoxytrityl Chloride

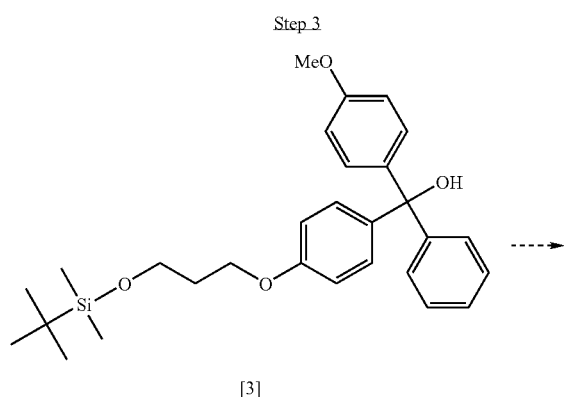

TLC System: Hexane/EtOAc [2:1]

A. 5.0 g (10.44 mmol) [3]

B. 18.2 mL (208 mmol) oxalyl chloride MW=126.9; Aldrich #32042-0

C. 150 mL Hexane

A 250 mL 3-neck round bottom flask was equipped with a cold-finger reflux/distillation condenser, magnetic stir bar, and two silicon rubber septa. (A) was suspended in (C) in the flask, and the flask was placed under argon and stirred. (B) was added to the stirring solution drop wise. Upon addition the suspended material dissolved and small bubbles formed in the flask. The reaction was refluxed overnight. The next morning the refluxing reaction consisted of a clear refluxing solution and a viscous orange-red oil on the bottom of the flask. The condenser was then set to distill and the hexanes and excess (B) removed by distillation. The remaining oil was placed under high vacuum resulting in 6.7 g of a foamed solid, used in the following reaction.

Theoretical Yield: 5.2 g

Actual Yield 5.2 g [100%]

3'-O-(4-Chlorophenyl)-Carbonyl-2'-Deoxythymidine

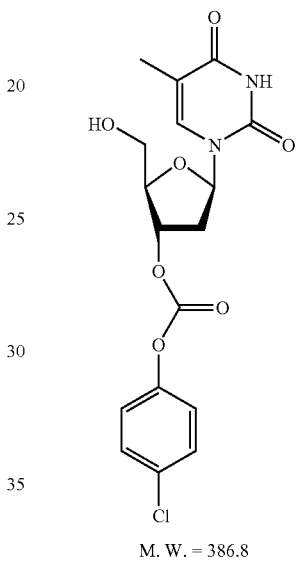

M. W. = 386.8

5'-O-(4,4'-Dimethoxytrityl)-2'-deoxythymidine (10.89 g, 20.0 mmol) was coevaporated from pyridine (3×40 mL), dissolved in pyridine (180 mL), and 4-chlorophenyl chloroformate (3.06 mL, 24.0 mmol) added with vigorous stirring. The mixture was stirred for 2 hours, solvent removed in vacuo, and the oily residue coevaporated with toluene (100 mL). The resulting oil was dissolved in dichloromethane (500 mL), extracted with sat. $NaHCO_3$ (250 mL) and brine (250 mL), dried over $MgSO_4$, and solvent evaporated to yield a viscous yellow oil. Purification by silica gel chromatography (0-2% ethanol in 100:0.1dichloromethane:triethylamine) yielded 3'-O-(4-chlorophenyl)-carbonyl-5'-O-(4,4'-dimethoxytrityl)-2'-deoxythymidine as a white, glassy solid (10.93 g, 78.2%).

Anal. $^1$H NMR (400 MHz, $CDCl_3$) δ 9.27 (1H, s, $H_3$), 7.63 (1H, s, $H_6$), 6.85-7.42 (17H, m), 6.54 (1H, m, $H_{1'}$), 5.43 (1H, m, $H_{3'}$), 4.32 (1H, m, $H_{4'}$), 3.78 (6H, s), 3.44-3.59 (2H, m, $H_{5'}$), 2.47-2.68 (2H, m, $H_{5',5''}$), 1.40 (3H, s); $^{13}$C NMR (100.5 MHz, $CDCl_3$) δ 163.7, 158.8, 152.7, 149.7, 149.2, 144.1, 135.1, 135.0, 131.7, 130.1, 130.0, 129.8, 129.6, 128.0, 127.2, 122.2, 113.3, 111.7, 87.3, 84.3, 83.6, 79.9, 63.6, 55.2, 37.8, 11.6; MS (FAB+) m/z 698 (M, 100).

To 3'-O-(4-chlorophenyl)-carbonyl-5'-O-(4,4'-dimethoxytrityl)-2'-deoxythymidine (2.50 g, 3.58 mmol) was added a 3% solution of trichloroacetic acid in dichloromethane (400 mL) with vigorous stirring. The mixture was stirred for 3 min before pyridine/methanol (1:1) was added drop wise until the red color of the DMT cation was quenched. The mixture was extracted with saturated $NaHCO_3$ (300 mL) and brine (300 mL), dried over MgSO$_4$, and solvent removed in vacuo. Purification of the resulting oil by silica gel chromatography (0-6% ethanol in dichloromethane) afforded the 3'-O-(4-Chlorophenyl)-Carbonyl-2'-Deoxythymidine.as a white powder (1.30 g, 92%);

Anal. Calcd. for C$_{17}$H$_{17}$ClN$_2$O$_7$: C, 51.5; H, 4.3; N, 7.1. Found: C, 51.3; H, 4.5; N, 7.0. $^1$H NMR (400 MHz, CDCl$_3$/d$_4$-MeOH) 9.57 (1H, s, H$_3$), 7.44 (1H, s, H$_6$), 7.25 (2H, d, J=8.8), 7.03 (2H, d, J=8.8), 6.17 (1H, m, H$_{1'}$), 5.27 (1H, m, H$_{3'}$), 4.17 (1H, m, H$_{4'}$), 3.83 (2H, m, H$_{5'}$), 2.42 (2H, m, H$_{2',2''}$), 1.80 (3H, s); $^{13}$C NMR (100.5 MHz, CDCl$_3$/d$_4$-MeOH) 164.1, 152.8, 150.6, 149.2, 136.7, 131.7, 129.6, 122.2, 111.4, 86.3, 84.8, 79.5, 62.4, 37.0, 12.5; MS (ESI+) m/z 397 (M+1, 100).

5'-O-4-((3-Propoxy)-tert-Butyldimethylsilane)-4''-Methoxytrityl-3'-O-(4-Chlorophenyl)-Carbonyl-2'-Deoxythymidine Step 4

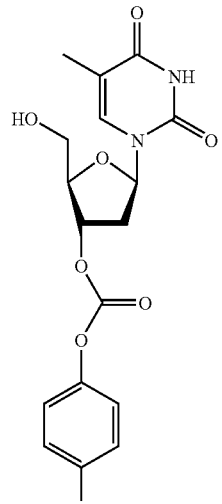

M. W. = 386.8

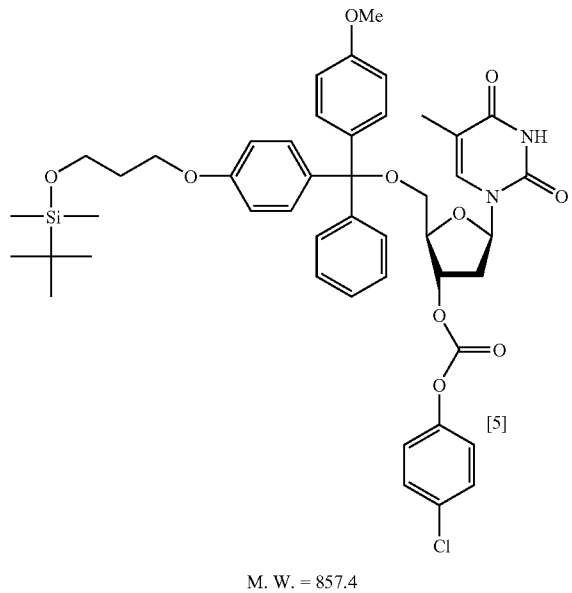

M. W. = 857.4

To 3'-O-(4-chlorophenyl)-carbonyl-2'-deoxythymidine (1.2 g, 3.1 mmol) in pyridine (35 mL) was added 4-((3-Propoxy)-tert-Butyldimethylsilane)-4'-Methoxytrityl Chloride (1.86 g, 3.75 mmol). The mixture was stirred for 4 h at which point the solvent was removed under reduced pressure. The residue was dissolved in dichloromethane, washed with 5% sodium carbonate and brine, dried (MgSO$_4$), and solvent removed in vacuo to yield a pale yellow oil. The 5'-O-4-((3-Propoxy)-tert-Butyldimethylsilane)-4''-Methoxytrityl-3'-O-(4-Chlorophenyl)-Carbonyl-2'-Deoxythymidine was isolated by silica gel chromatography using 1-4% methanol/dichloromethane as eluant as a pale yellow glassy solid (2.4 g, 90.0%); MS (FAB+) m/z 743 (M, 100).

5'-O-4-(3-Hydroxypropyl)-4''-Methoxytrityl-3'-O-(4-Chlorophenyl)-Carbonyl-2'-Deoxythymidine Step 5

[5] ---->

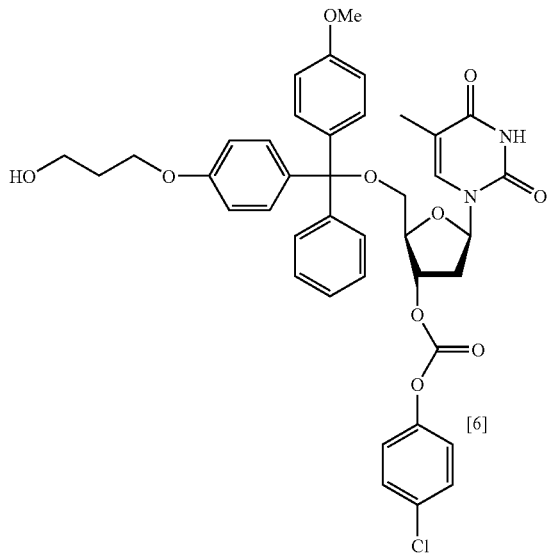

M. W. = 743.2

5'-O-4-((3-Propoxy)-tert-butyldimethylsilane)-4''-methoxytrityl-3'-O-(4-chlorophenyl)-carbonyl-2'-deoxythymidine (2.4 g, 2.8 mmol) was dissolved in anhydrous pyridine (75 mL) using a magnetic stirrer. The flask was kept anhydrous under argon and cooled in an ice/water bath. Hydrogen fluoride pyridine (100 μL) Fluka cat# 47586 was dissolved in 10 mL of anhydrous pyridine and added to the stirring flask. The reaction was allowed to stir for 30 min then evaporated to a rust brown oil. The residue was dissolved in dichloromethane, washed with 5% sodium carbonate and brine, dried (MgSO$_4$), and solvent removed in vacuo to yield a dark yellow oil. The 5'-O-4-(3-Hydroxypropyl)-4''-Methoxytrityl-3'-O-(4-Chlorophenyl)-Carbonyl-2'-Deoxythymidine was isolated by silica gel chromatography using 0-3% methanol/dichloromethane as eluant as a pale yellow glassy solid (2.4 g, 90.0%); MS (FAB+) m/z 859 (M, 100).

5'-O-4-(3-propyloxy(2-Cyanoethyl N,N-diisopropylphosphoramidite))-4"-Methoxytrityl-3'-O-(4Chlorophenyl)-Carbonyl-2'-Deoxythymidine Step 6

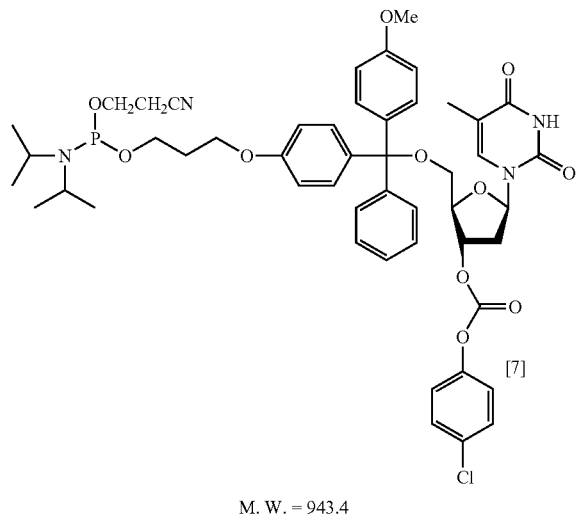

M. W. = 943.4

5'-O-4-(3-Hydroxypropyl)-4"-Methoxytrityl-3'-O-(4-Chlorophenyl)-Carbonyl-2'-Deoxythymidine 3.7 g (5.0 mmol) and tetrazole (175 mg, 2.50 mmol) were dried under vacuum for 24 h then dissolved in dichloromethane (100 mL). 2-Cyanoethyl N,N,N',N'-tetraisopropylphosphorodiamidite (2.06 mL, 6.50 mmol) was added in one portion and the mixture stirred over 1 h. The reaction mixture was washed with sat. NaHCO$_3$ (150 mL) and brine (150 mL), dried over MgSO$_4$, and applied directly to the top of a silica column equilibrated with hexanes. The dichloromethane was flashed off the column with hexanes, and the product eluted as a mixture of diastereoisomers using 1:1 hexanes: ethyl acetate then ethyl acetate. After evaporation of solvents in vacuo and coevaporation with dichloromethane, product was isolated as friable, white, glassy solids in 75% yield; $^{31}$P NMR (162.0 MHz, CDCl$_3$) 148.89, 148.85; MS (FAB+) m/z 945 (FAB−) m/z 943

It will be apparent to one of skill in the art that the series of syntheses described above may be altered to employ analogous starting materials that react in a similar manner to give analogous products, and that such alteration of the synthesis is within ordinary skill in the art. For example, thymidine may be replaced with N-4-dimethoxy trityl-2'-deoxycytidine in step 4 to give 5'-O-4-(3-propyloxy-(2-cyanoethyl N, N-diisopropyl-phosphoramidite))-4"-methoxytrityl-3'-O-(4-chlorophenyl)-carbonyl- N-4-dimethoxytrityl-2'-deoxycytidine as the final product. As another example, in step 2, the (3-bromopropoxy)-tert-butyldimethylsilane may be replaced with (4-bromobutoxy)-tert-butyldimethylsilane to give 4-((4-Butoxy)-tert-butyldimethylsilane)-4'-methoxytrityl alcohol the product of step 2. As another example, it will be appreciated that the nucleoside moiety may be bound to the triaryl methyl linker group via either the 3'-OH or the 5'-OH. Such a modification will be accomplished by reacting a 5'-O-protected nucleoside with the trityl linker under conditions that enhance the rate of trityl reaction with secondary hydroxyls such as the addition of an acylation catalyst like N,N-dimethlyaminopyridine or silver salts as well as other techniques well known to one skilled in the art.

Furthermore, in the reaction designated as "Step 1", above, the starting materials may be modified to yield a product wherein one or more of the phenyl (or substituted phenyl) rings is replaced by an alternate aromatic ring moiety, such as substituted or unsubstituted aromatic groups such as phenyl, biphenyl, naphthanyl, indolyl, pyridinyl, pyrrolyl, thiophenyl, furanyl, annulenyl, quinolinyl, anthracenyl, and the like. Such products may then be used as alternative starting materials in the reaction designated "Step 2" (and so on through the rest of the described syntheses) to give a triaryl methyl-modified nucleotide monomer, above.

As shown in the reaction designated (XII), below, the 5'-linked molecules can then be reacted with a support having a reactive moiety such as a hydroxyl group, thiol group, or amino group, wherein the support is suitable for use for polynucleotide synthesis.

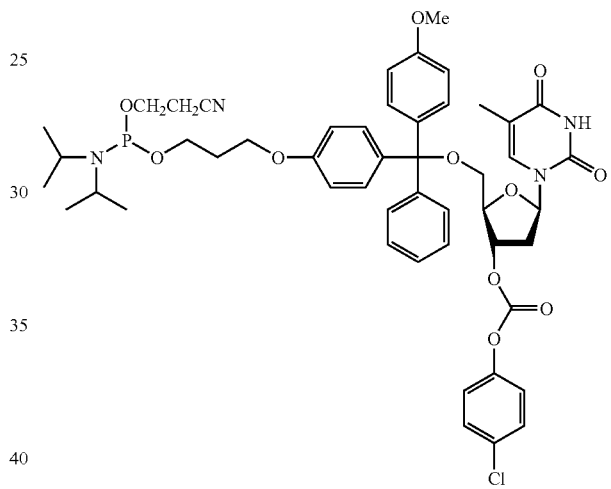

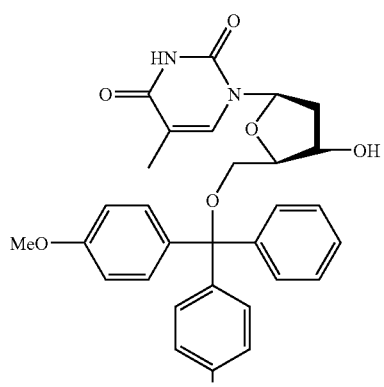

-continued

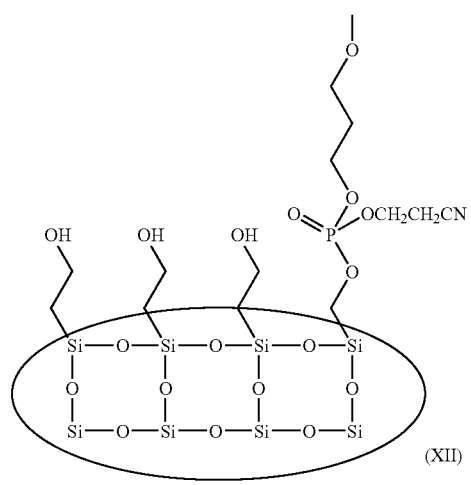

(XII)

The 3'-hydroxyl of the nucleoside moiety may then be used as a starting point for performing cycles of a polynucleotide synthesis reaction to give a product in which a polynucleotide strand is bound to the substrate via the trityl group. An example of such a product is shown in the reaction designated (XIII), below, in which an oligonucleotide that is four nucleotides long has been synthesized and is bound to the substrate via the trityl moiety.

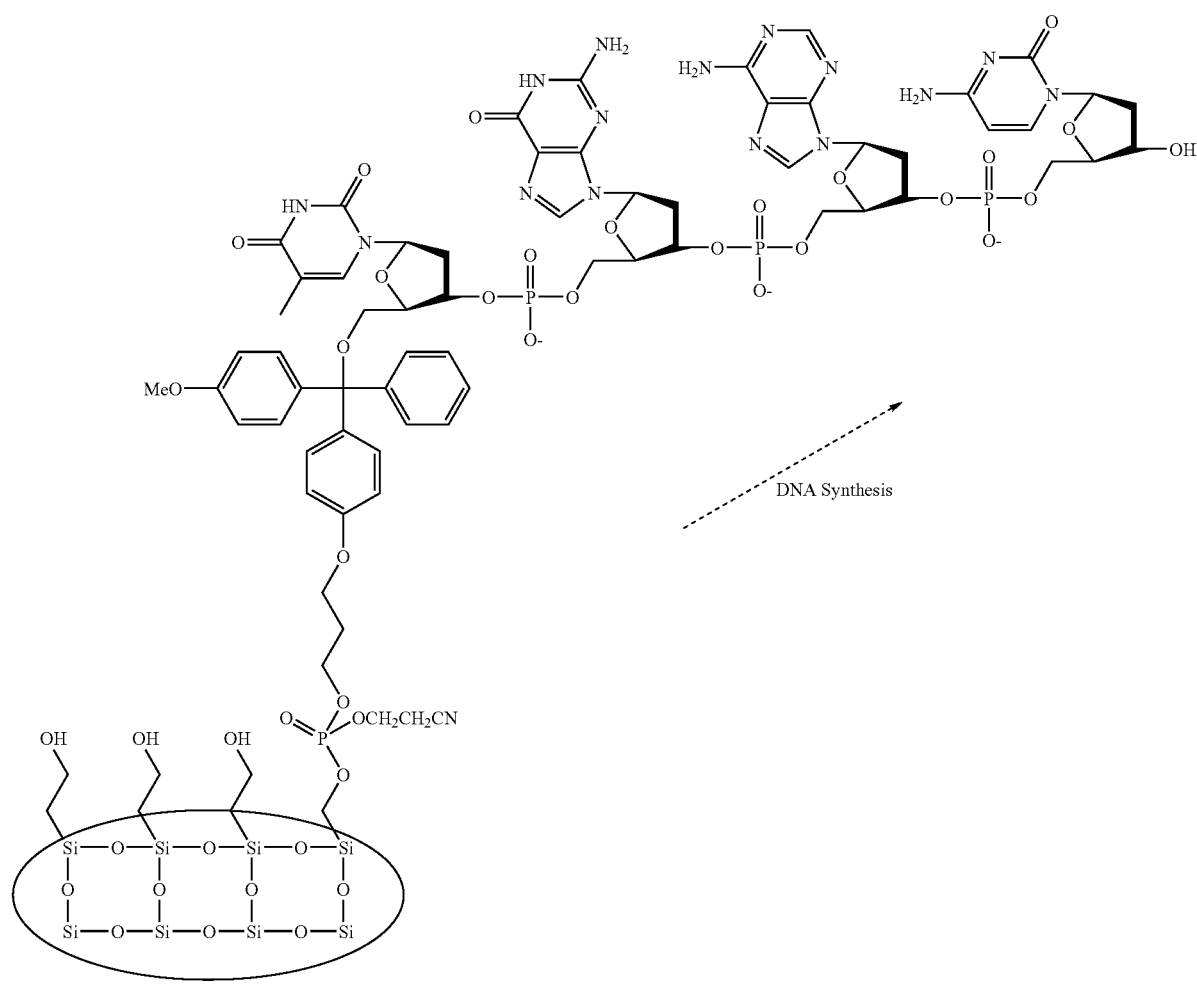

(XIII)

Once the synthesis is complete, the polynucleotide can be released from the support with mild acid. The products of such reaction are shown in the structures designated (XIV), below. The polynucleotide may then be, e.g. subjected to further analysis or used as desired. In certain embodiments, a strand of DNA is synthesized on the support, followed by releasing the DNA off of the support using glacial acetic acid at room temperature for 90 minutes. The resulting released DNA may then be analyzed by HPLC or capillary electrophoresis (CE).

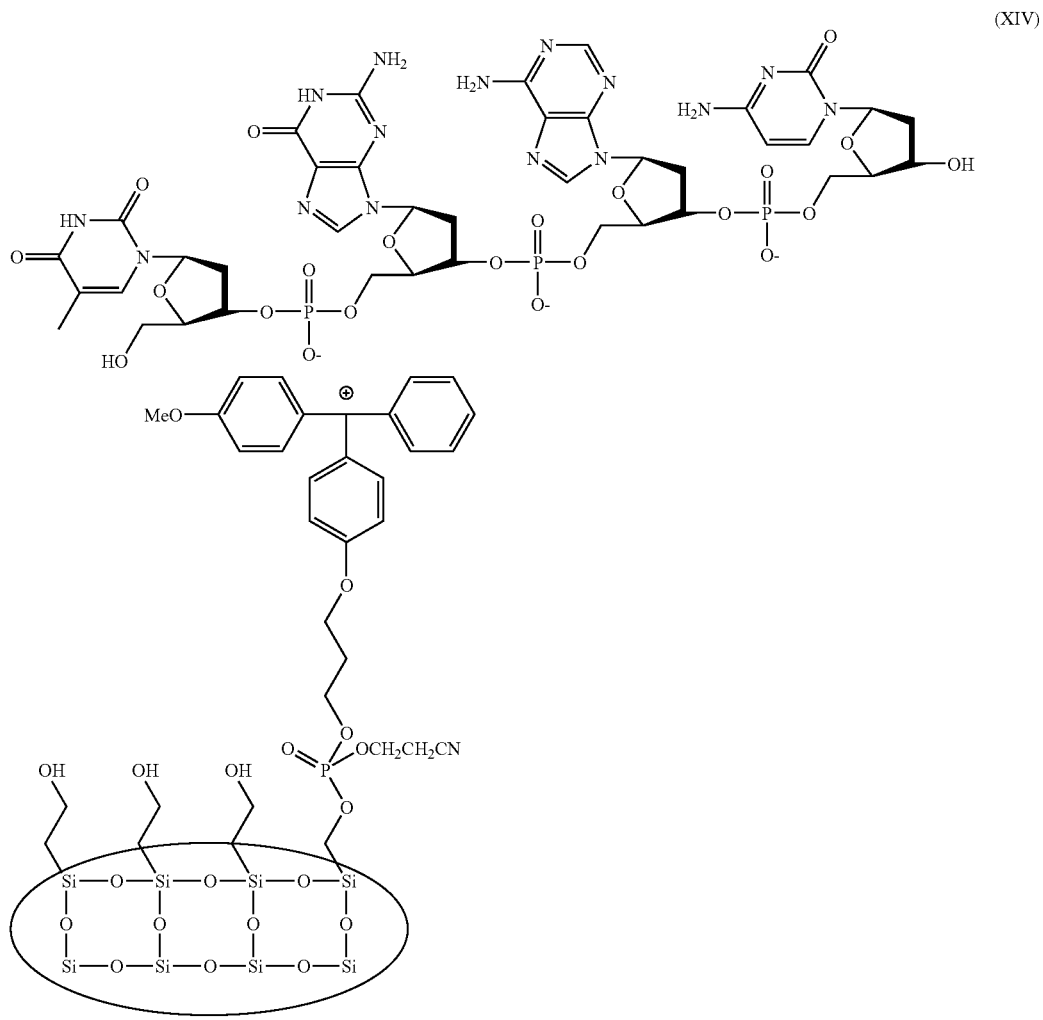

(XIV)

While the foregoing embodiments of the invention have been set forth in considerable detail for the purpose of making a complete disclosure of the invention, it will be apparent to those of skill in the art that numerous changes may be made in such details without departing from the spirit and the principles of the invention. Accordingly, the invention should be limited only by the following claims.

All patents, patent applications, and publications mentioned herein are hereby incorporated by reference in their entireties.

What is claimed is:

1. A compound having the structure (I)

Phos-Cgp-Trl-Cgp'-Nucl    (I)

wherein:

Phos is a reactive phosphorus group which specifically reacts with a reactive group on a solid support to produce a phosphorous containing linkage group, Trl is a triaryl methyl linker group having three aryl groups, wherein each of the three aryl groups are bound to a central methyl carbon, and at least one of said three aryl groups has one or more substituents, wherein one of said substituents is bound to Cgp and the central methyl carbon is bound to Cgp', Cgp is a linking group linking the reactive phosphorus group and the triaryl methyl linker group, or is a bond linking the reactive phosphorus group and the triaryl methyl linker group, Nucl is a nucleoside moiety, and Cgp' is a linking group linking the nucleoside moiety at the 3'O or the 5'O and the triaryl methyl linker group, or is a bond linking the nucleoside moiety at the 3'O or the 5'O and the central methyl carbon of the triaryl methyl linker group; and wherein the reactive phosphorous group has the structure (VI)

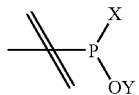
(VI)

wherein:
the broken line indicates the bond to the Cgp;
X is selected from a halo group and a secondary amino group; and
Y is selected from hydrido, hydrocarbyl, and substituted hydrocarbyl.

2. The compound of claim 1, wherein the triaryl methyl linker group has the structure (IV)

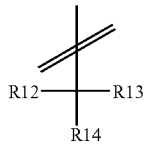
(IV)

wherein the broken line represents the bond to the linking group denoted Cgp' in structure (I), and
wherein $R_{12}$, $R_{13}$, and $R_{14}$ are independently selected from unsubstituted and substituted aryl groups, provided that one of $R_{12}$, $R_{13}$, and $R_{14}$ is substituted by being bound to the reactive phosphorus group via the Cgp group.

3. The compound of claim 2, wherein $R_{12}$, $R_{13}$, and $R_{14}$ are independently selected from substituted phenyl and unsubstituted phenyl, provided that one of $R_{12}$, $R_{13}$, and $R_{14}$ is substituted by being bound to the reactive phosphorus group via the Cgp group.

4. The compound of claim 2, wherein $R_{12}$, $R_{13}$, and $R_{14}$ are independently selected from unsubstituted or substituted aryl groups selected from phenyl, biphenyl, naphthanyl, indolyl, pyridinyl, pyrrolyl, 2-thienyl, 3-thienyl, furanyl, annulenyl, quinolinyl, and anthracenyl, provided that one of $R_{12}$, $R_{13}$, and $R_{14}$ is substituted by being bound to the reactive phosphorous group via the Cgp group.

5. The compound of claim 4, wherein at least one of $R_{12}$, $R_{13}$, and $R_{14}$ is selected from naphthanyl, indolyl, pyridinyl, pyrrolyl, 2-thienyl, 3-thienyl, furanyl, annulenyl, quinolinyl, and anthracenyl, provided that one of $R_{12}$, $R_{13}$, and $R_{14}$ is substituted by being bound to the reactive phosphorous group via the Cgp group.

6. The compound of claim 2, wherein $R_{12}$, $R_{13}$, and $R_{14}$ are independently selected from phenyl, methoxyphenyl, dimethoxyphenyl, trimethoxyphenyl, and furanyl, provided that one of $R_{12}$, $R_{13}$, and $R_{14}$ is substituted by being bound to the reactive phosphorous group via the Cgp group.

7. The compound of claim 1, wherein the linking group denoted Cgp' comprises a polynucleotide moiety.

8. The compound of claim 1, wherein X is a secondary amino group having the structure —$NQ_1Q_2$; in which $Q_1$ and $Q_2$ are independently selected from the group consisting of alkyl, aryl, aralkyl, cycloalkyl, alkenyl, cycloalkenyl, alkynyl, and cycloalkynyl.

9. The compound of claim 1, wherein Y is selected from alkyl, lower alkyl, alkenyl, benzyl, substituted benzyl, aryl, aralkyl, cycloalkyl, electron-withdrawing β-substituted alkyl, electron-withdrawing β-substituted ethyl; electron-withdrawing substituted phenyl; and electron-withdrawing substituted phenylethyl.

10. The compound of claim 1, wherein X is a diisopropyl amino group and Y is selected from methyl, benzyl, substituted benzyl, β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, β-thiobenzoylethyl, 1,1,1,3,3,3-hexafluoro-2-propyl, 2,2,2-trichloroethyl,p-nitrophenylethyl, p-cyanophenyl-ethyl, 9-fluorenylmethyl, 1,3-dithionyl-2-methyl, 2-(trimethylsilyl)ethyl, 2-methylthioethyl, 2-(diphenylphosphino)-ethyl, 1-methyl-1-phenylethyl, 3-buten-1-yl, 4-(trimethylsilyl)-2-buten-1-yl, cinnamyl, α-methylcinnamyl, and 8-quinolyl.

11. A method comprising:
(a) providing a solid support having an available hydroxyl, amino, or thio reactive group bound thereto;
(b) contacting said solid support with a compound having the structure (I)

Phos-Cgp-Trl-Cgp'-Nucl     (I)

wherein:
Phos is a reactive phosphorus group which specifically reacts with a reactive group on a solid support to produce a phosphorous containing linkage group,
Trl is a triaryl methyl linker group having three aryl groups, wherein each of the three aryl groups are bound to a central methyl carbon, and at least one of said three aryl groups has one or more substituents, wherein one of said substituents is bound to Cgp and the central methyl carbon is bound to Cgp',
Cgp is a linking group linking the reactive phosphorus group and the triaryl methyl linker group, or is a bond linking the reactive phosphorus group and the triaryl methyl linker group,
Nucl is a nucleoside moiety, and
Cgp' is a linking group linking the nucleoside moiety at the 3'O or the 5'O to the triaryl methyl linker group, or is a bond linking the nucleoside moiety at the 3'O or the 5'O to the central methyl carbon of the triaryl methyl linker group; and
wherein the reactive phosphorous group has the structure (VI)

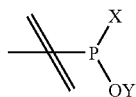
(VI)

wherein:
the broken line indicates the bond to the Cgp;
X is selected from a halo group and a secondary amino group; and
Y is selected from hydrido, hydrocarbyl, or substituted hydrocarbyl;
under conditions and for a time sufficient for said reactive phosphorous group to covalently bond to said solid support to produce a functionalized solid support.

12. The method of claim 11, wherein the available reactive group is selected from hydroxyl, and thio.

13. The method of claim 12, wherein X is a secondary amino group having the structure —$NQ_1Q_2$; in which $Q_1$ and $Q_2$ are independently selected from the group consisting of alkyl, aryl, aralkyl, cycloalkyl, alkenyl, cycloalkenyl, alkynyl, and cycloalkynyl.

14. The method of claim 12, wherein Y is selected from alkyl, lower alkyl, alkenyl, benzyl, substituted benzyl, aryl, aralkyl, cycloalkyl, electron-withdrawing β-substituted alkyl, electron-withdrawing β-substituted ethyl; electron-withdrawing substituted phenyl; and electron-withdrawing substituted phenylethyl.

15. The method of claim 11, wherein the nucleoside moiety has a hydroxyl protecting group bound thereto.

16. The method of claim 15, said method further comprising contacting the functionalized solid support with a combined deprotection/oxidation agent.

17. The method of claim 16, wherein the combined deprotection/oxidation agent comprises an alpha effect nucleophile.

18. The method of claim 11, wherein the triaryl methyl linker group has the structure (IV)

(IV)

wherein the broken line represents the bond via which the triaryl methyl linker group is bound to the nucleoside moiety, and wherein $R_{12}$, $R_{13}$, and $R_{14}$ are independently selected from unsubstituted and substituted aryl groups, provided that one of $R_{12}$, $R_{13}$ and $R_{14}$ is substituted by being bound to the reactive phosphorus group.

19. The method of claim 18, wherein $R_{12}$, $R_{13}$, $R_{14}$ are independently selected from substituted phenyl and unsubstituted phenyl, provided that one of $R_{12}$, $R_{13}$, and $R_{14}$ is substituted by being bound to the reactive phosphorus group.

20. The method of claim 18, wherein $R_{12}$, $R_{13}$, and $R_{14}$ are independently selected from unsubstituted or substituted aryl groups selected from phenyl, biphenyl, naphthanyl, indolyl, pyridinyl, pyrrolyl, 2-thienyl, 3-thienyl, furanyl, annulenyl, quinolinyl, and anthracenyl.

21. The method of claim 18, wherein at least one of $R_{12}$, $R_{13}$, and $R_{14}$ is selected from naphthanyl, indolyl, pyridinyl, pyrrolyl, 2-thienyl, 3-thienyl, furanyl, annulenyl, quinolinyl, and anthracenyl.

* * * * *